(12) United States Patent
Mayou et al.

(10) Patent No.: US 9,953,542 B2
(45) Date of Patent: Apr. 24, 2018

(54) ADAPTIVE INTERFACE FOR CONTINUOUS MONITORING DEVICES

(71) Applicant: DexCom, Inc., San Diego, CA (US)

(72) Inventors: Phil Mayou, San Diego, CA (US); Naresh C. Bhavaraju, San Diego, CA (US); Leif N. Bowman, Livermore, CA (US); Alexandra Lynn Carlton, San Marcos, CA (US); Laura J. Dunn, San Diego, CA (US); Katherine Yerre Koehler, San Diego, CA (US); Aarthi Mahalingam, San Diego, CA (US); Eli Reihman, San Diego, CA (US); Peter C. Simpson, Cardiff, CA (US)

(73) Assignee: DexCom, Inc., San Diego, CA (US)

( * ) Notice: Subject to any disclaimer, the term of this patent is extended or adjusted under 35 U.S.C. 154(b) by 388 days.

(21) Appl. No.: 14/525,622

(22) Filed: Oct. 28, 2014

(65) Prior Publication Data

US 2015/0119655 A1   Apr. 30, 2015

Related U.S. Application Data

(60) Provisional application No. 61/898,300, filed on Oct. 31, 2013.

(51) Int. Cl.
*A61B 5/02* (2006.01)
*G09B 19/00* (2006.01)
(Continued)

(52) U.S. Cl.
CPC .................. *G09B 5/02* (2013.01); *A61B 5/01* (2013.01); *A61B 5/1112* (2013.01);
(Continued)

(58) Field of Classification Search
CPC ....... A61B 5/01; A61B 5/1112; A61B 5/1118; A61B 5/14532; A61B 5/14552;
(Continued)

(56) References Cited

U.S. PATENT DOCUMENTS

| 5,901,246 A | 5/1999 | Hoffberg et al. |
| 7,260,480 B1 | 8/2007 | Brown |

(Continued)

FOREIGN PATENT DOCUMENTS

| WO | WO 2011-132097 | 10/2011 |
| WO | WO 2012-122196 | 9/2012 |

OTHER PUBLICATIONS

Gonder-Fredenck et al., 2011. J. Diabetes Science & Technology 5(6):1387-1395. Closed-Loop Glucose Control: Psychological and Behavioral Considerations.
(Continued)

*Primary Examiner* — Navin Natnithithadha
(74) *Attorney, Agent, or Firm* — Knobbe Martens Olson & Bear LLP

(57) ABSTRACT

Systems and methods that continuously adapt aspects of a continuous monitoring device based on collected information to provide an individually tailored configuration are described. The adaptations may include adapting the user interface, the alerting, the motivational messages, the training, and the like. Such adaptation can allow a patient to more readily identify and understand the information provided by/via the device.

22 Claims, 7 Drawing Sheets

(51) Int. Cl.
    *A61B 5/01*     (2006.01)
    *G09B 5/02*     (2006.01)
    *A61B 5/1455*     (2006.01)
    *A61B 5/00*     (2006.01)
    *A61B 5/11*     (2006.01)
    *A61B 5/145*     (2006.01)
    *A61B 5/16*     (2006.01)
    *H04L 29/08*     (2006.01)
    *G06F 19/00*     (2018.01)

(52) U.S. Cl.
    CPC ........ *A61B 5/1118* (2013.01); *A61B 5/14532* (2013.01); *A61B 5/14552* (2013.01); *A61B 5/165* (2013.01); *A61B 5/7275* (2013.01); *A61B 5/7282* (2013.01); *A61B 5/742* (2013.01); *A61B 5/746* (2013.01); *G06F 19/3406* (2013.01); *G06F 19/3418* (2013.01); *G06F 19/3487* (2013.01); *G09B 19/00* (2013.01); *H04L 67/12* (2013.01)

(58) Field of Classification Search
    CPC ..... A61B 5/165; A61B 5/7275; A61B 5/7282; A61B 5/742; A61B 5/746; G06F 19/3406; G06F 19/3418; G06F 19/3487; G09B 19/00; G09B 5/02; H04L 67/12
    USPC .......................................... 600/309, 345–366
    See application file for complete search history.

(56) References Cited

U.S. PATENT DOCUMENTS

| | | | |
|---|---|---|---|
| 7,725,419 B2 | 5/2010 | Lee et al. | |
| 8,046,313 B2 | 10/2011 | Hoffberg et al. | |
| 8,069,135 B2 | 11/2011 | Fletcher et al. | |
| 8,160,900 B2 * | 4/2012 | Taub | A61B 5/14532 340/526 |
| 8,340,666 B2 | 12/2012 | Ramer et al. | |
| 8,359,019 B2 | 1/2013 | Ramer et al. | |
| 8,429,103 B1 | 4/2013 | Aradhye et al. | |
| 8,487,758 B2 | 7/2013 | Istoc | |
| 8,706,520 B2 | 4/2014 | Reinke et al. | |
| 9,226,702 B2 | 1/2016 | Ecoff et al. | |
| 2003/0028498 A1 | 2/2003 | Hayes-Roth | |
| 2003/0134259 A1 | 7/2003 | Adams | |
| 2003/0208113 A1 | 11/2003 | Mault et al. | |
| 2004/0044272 A1 | 3/2004 | Moerman et al. | |
| 2007/0067251 A1 | 3/2007 | Brown | |
| 2007/0169021 A1 | 7/2007 | Huynh et al. | |
| 2008/0027292 A1 | 1/2008 | Rosman et al. | |
| 2010/0099974 A1 | 4/2010 | Desai | |
| 2010/0131482 A1 | 5/2010 | Linthicum et al. | |
| 2010/0131498 A1 | 5/2010 | Linthicum et al. | |
| 2011/0047108 A1 | 2/2011 | Chakrabarty et al. | |
| 2011/0050428 A1 | 3/2011 | Istoc | |
| 2011/0124996 A1 * | 5/2011 | Reinke | A61M 5/14248 600/365 |
| 2011/0161107 A1 | 6/2011 | Goldberg | |
| 2011/0172499 A1 | 7/2011 | Simons-Nikolova | |
| 2012/0165639 A1 | 6/2012 | Engelhardt et al. | |
| 2012/0266251 A1 | 10/2012 | Birtwhistle et al. | |
| 2013/0044042 A1 | 2/2013 | Olsson et al. | |
| 2014/0066735 A1 | 3/2014 | Engelhardt et al. | |
| 2014/0099616 A1 | 4/2014 | Hussam | |
| 2015/0118658 A1 * | 4/2015 | Mayou | A61B 5/14552 434/127 |
| 2015/0118668 A1 * | 4/2015 | Mayou | A61B 5/14552 434/236 |
| 2015/0119668 A1 * | 4/2015 | Mayou | A61B 5/14552 600/365 |
| 2015/0120317 A1 * | 4/2015 | Mayou | A61B 5/14552 705/2 |

OTHER PUBLICATIONS

Ritholz et al., 2010. Diabetic Medicine 27:1060-1065. Education and Psychological Aspects / Psychosocial factors associated with use of continue glucose monitoring.

\* cited by examiner

ADAPTIVE INTERFACE FOR CONTINUOUS MONITORING DEVICES

INCORPORATION BY REFERENCE TO RELATED APPLICATION

Any and all priority claims identified in the Application Data Sheet, or any correction thereto, are hereby incorporated by reference under 37 CFR 1.57. This application claims the benefit of U.S. Provisional Application No. 61/898,300 filed Oct. 31, 2013. The aforementioned application is incorporated by reference herein in its entirety, and is hereby expressly made a part of this specification.

FIELD OF THE INVENTION

The present development relates generally to medical devices such as a continuous glucose sensor, including systems and methods for adaptive interface processing of sensor data.

BACKGROUND

Diabetes mellitus is a disorder in which the pancreas cannot create sufficient insulin (Type I or insulin dependent) and/or in which insulin is not effective (Type 2 or non-insulin dependent). In the diabetic state, the victim suffers from high glucose, which may cause an array of physiological derangements (for example, kidney failure, skin ulcers, or bleeding into the vitreous of the eye) associated with the deterioration of small blood vessels. A hypoglycemic reaction (low glucose) may be induced by an inadvertent overdose of insulin, or after a normal dose of insulin or glucose-lowering agent accompanied by extraordinary exercise or insufficient food intake.

Conventionally, a person with diabetes carries a self-monitoring blood glucose (SMBG) monitor, which typically requires uncomfortable finger pricks to obtain blood samples for measurement. Due to the lack of comfort and convenience associated with finger pricks, a person with diabetes normally only measures his or her glucose levels two to four times per day. Unfortunately, time intervals between measurements can be spread far enough apart that the person with diabetes finds out too late of a hyperglycemic or hypoglycemic condition, sometimes incurring dangerous side effects. It is not only unlikely that a person with diabetes will take a timely SMBG value, it is also likely that he or she will not know if his or her blood glucose value is going up (higher) or down (lower) based on conventional methods. Diabetics thus may be inhibited from making educated insulin therapy decisions.

Another device that some diabetics use to monitor their blood glucose is a continuous analyte sensor. A continuous analyte sensor typically includes a sensor that is placed subcutaneously, transdermally (e.g., transcutaneously), or intravascularly. The sensor measures the concentration of a given analyte within the body, and generates a raw signal that is transmitted to electronics associated with the sensor. The raw signal is converted into an output value that is displayed on a display. The output value that results from the conversion of the raw signal is typically expressed in a form that provides the user with meaningful information, such as blood glucose expressed in mg/dL. Unfortunately, wide spread adoption of continuous analyte sensors has been hindered because of the "one size fits all" approach to system designs thus far.

SUMMARY

A system that continuously adapts based on collected information to provide an individually tailored configuration is believed to improve widespread adoption by adaptively and interactively improving healthcare assistance for chronic management of disease in an ambulatory setting. The adaptations may include adapting the user interface, the alerting, the motivational messages, the training, and the like. Such adaptation can allow a patient to more readily identify and understand the information provided by/via the device.

In a first innovative aspect, a method for adaptive configuration of an analyte monitoring device is provided. The method includes transmitting a first report of physiological information of a subject using a first reporting format, wherein the first reporting format comprises a first reporting format characteristic. The method further includes determining at least one of behavioral or contextual information comprising at least one behavioral or contextual characteristic for the subject. The method also includes comparing the at least one behavioral and/or contextual characteristic with one or more behavioral or contextual criteria. The method additionally includes adjusting the reporting format based at least in part on the comparing, wherein the reporting format comprises a second reporting format characteristic that is different from the first reporting format characteristic. The method further includes transmitting a second report of physiological information using the second reporting format.

In a generally applicable embodiment (i.e., independently combinable with any of the aspects or embodiments identified herein) of the first aspect, the first report comprises a trend graph of the physiological information over a period of time.

In a generally applicable embodiment (i.e., independently combinable with any of the aspects or embodiments identified herein) of the first aspect, determining the behavioral or contextual information includes receiving a message from a sensor including data associated with a patient, identifying a characteristic extractor based on the message and the sensor, generating, via the identified characteristic extractor, the at least one behavioral or contextual characteristic based on the received message, and associating the generated characteristic with the behavioral or contextual information.

In a generally applicable embodiment (i.e., independently combinable with any of the aspects or embodiments identified herein) of the first aspect, comparing the characteristic with one or more behavioral or contextual criteria includes comparing the characteristic with a behavioral or contextual criteria associated with a goal.

In a generally applicable embodiment (i.e., independently combinable with any of the aspects or embodiments identified herein) of the first aspect, comparing the characteristic with one or more behavioral or contextual criteria comprises comparing the characteristic with a behavioral or contextual criteria associated with an interface adaptation. In some implementations, the interface adaptation comprises at least one of an alert frequency, an alert volume, an alert tone, a display font, a display font size, a display font color, a message delivery address, a message delivery telephone number, a listing of menu items, or an operational setting for the analyte monitoring device.

In a generally applicable embodiment (i.e., independently combinable with any of the aspects or embodiments identified herein) of the first aspect, the method further includes transmitting a message identifying the adjustment, and upon receipt of a confirmation of the adjustment, activating the second reporting format for subsequent reporting, as well as, upon receipt of a denial of the adjustment or no response to the message, activating the first reporting format for subsequent reporting.

In a generally applicable embodiment (i.e., independently combinable with any of the aspects or embodiments identified herein) of the first aspect, the first report is transmitted to a common destination as the second report.

In a generally applicable embodiment (i.e., independently combinable with any of the aspects or embodiments identified herein) of the first aspect, the first report is transmitted to a first destination and the second report is transmitted to a second destination.

In a second innovative aspect, a method of identifying adaptation information for an individual is provided. The method includes capturing values from pre-identified inputs, the values indicating a behavior or context associated with a physiological condition for the individual. The method further includes periodically storing additional values received from the pre-identified inputs, wherein a record of user-specific pre-identified input values is created. The method further includes periodically determining behavioral or contextual information about the individual based on the record of user-specific pre-identified input values.

In a generally applicable embodiment (i.e., independently combinable with any of the aspects or embodiments identified herein) of the second aspect, the method further includes transmitting the determined behavioral or contextual information about the patient.

In a generally applicable embodiment (i.e., independently combinable with any of the aspects or embodiments identified herein) of the second aspect, transmitting includes transmitting to a continuous monitoring device, a patient record system, a smartphone, or a social media internet site.

In a generally applicable embodiment (i.e., independently combinable with any of the aspects or embodiments identified herein) of the second aspect, the pre-identified inputs include at least one of a glucometer, a thermometer, an accelerometer, a camera, a microphone, a query processing engine, an electronic device configured for machine-to-machine communication, or an electronic patient record.

In a generally applicable embodiment (i.e., independently combinable with any of the aspects or embodiments identified herein) of the second aspect, periodically storing additional values comprises storing a timestamp indicating when a specific additional value was stored.

In a generally applicable embodiment (i.e., independently combinable with any of the aspects or embodiments identified herein) of the second aspect, the physiological condition comprises one or more of diabetes, obesity, malnutrition, hyperactivity, depression, or fertility.

In a generally applicable embodiment (i.e., independently combinable with any of the aspects or embodiments identified herein) of the second aspect, determining behavioral or contextual information about the individual includes selecting one of a plurality of pre-identified input values included in the record, and identifying one or more behavior or context based on a comparison of the selected input value and the input providing the selected value with an identification value associated with a plurality of behaviors or contexts.

In a generally applicable embodiment (i.e., independently combinable with any of the aspects or embodiments identified herein) of the second aspect, determining behavioral or contextual information about the individual comprises processing the pre-defined input values included in the record.

In a generally applicable embodiment (i.e., independently combinable with any of the aspects or embodiments identified herein) of the second aspect, processing the values comprises identifying a trend for the values.

In a third innovative aspect, a method of adaptive goal setting for an individual is provided. The method includes obtaining first behavioral or contextual information associated with the individual. The method further includes obtaining second behavioral or contextual information associated with a plurality of individuals having a common characteristic with the individual. The method includes generating one or more behavioral or contextual criteria for the goal based on the obtained first information and the obtained second information. The method also includes generating the goal based on the generated criteria.

In a generally applicable embodiment (i.e., independently combinable with any of the aspects or embodiments identified herein) of the third aspect, the method also includes providing a predetermined goal including at least one behavioral or contextual criteria, and wherein generating the goal comprises modifying the at least one behavioral or contextual criteria of the predetermined goal based on the generated one or more behavioral or contextual criteria.

In a generally applicable embodiment (i.e., independently combinable with any of the aspects or embodiments identified herein) of the third aspect, the method also includes providing the generated goal for presentation via a human detectable interface and receiving a message activating the goal.

In a fourth innovative aspect, a method of adaptive guidance is provided. The method includes identifying a need related to training need or requested guidance based on behavioral/contextual information for the user. The method also includes providing training or guidance in response to the identified need, wherein the training or guidance is based on physiological information in conjunction with the behavioral/contextual information for the user.

In a generally applicable embodiment (i.e., independently combinable with any of the aspects or embodiments identified herein) of the fourth aspect, the behavioral or contextual information includes a structured query or a natural language query.

In a generally applicable embodiment (i.e., independently combinable with any of the aspects or embodiments identified herein) of the fourth aspect, the method also includes receiving feedback associated with the training or guidance and re-processing the training or guidance in further consideration of the received feedback.

In a fifth innovative aspect, an integrated system for monitoring a glucose concentration in a host and for delivering insulin to the host is provided. The system includes a continuous glucose sensor, wherein the continuous glucose sensor is configured to substantially continuously measure a glucose concentration in the host, and to provide continuous sensor data associated with the glucose concentration in the host. The system further includes an insulin delivery device configured to deliver insulin to the host, wherein the insulin delivery device is operably connected to the continuous glucose sensor. The system also includes a processor module configured to perform, in whole or in part, any one of the four innovative methods described above.

In a sixth innovative aspect, an electronic device for monitoring a glucose concentration in a host is provided. The device includes a continuous glucose sensor, wherein the continuous glucose sensor is configured to substantially continuously measure a glucose concentration in the host, and to provide continuous sensor data associated with the glucose concentration in the host. The device further includes a processor module configured to perform, in whole or in part, any one of the four innovative methods described above.

In a seventh innovative aspect, an electronic device for delivering insulin to a host is provided. The device includes an insulin delivery device configured to deliver insulin to the host, wherein the insulin delivery device is operably connected to the continuous glucose sensor. The device also includes a processor module configured to perform, in whole or in part, any one of the four innovative methods described above.

In an eighth innovative aspect, a system for adaptive configuration of an analyte monitoring device is provided. The system includes an input receiver configured to receive at least one of context information, behavior information, or physiological information for a user over a period of time. The system includes an input processor configured to identify a context or behavior based at least in part on the information received over time. The system further includes an adaptation engine configured to determine an adaptation for the analyte monitoring device based on the identified context or behavior.

Any of the features of an embodiment of the first, second, third, fourth, fifth, sixth, seventh or eighth aspects is applicable to all aspects and embodiments identified herein. Moreover, any of the features of an embodiment of the first, second, third, fourth, sixth, seventh or eighth aspects is independently combinable, partly or wholly with other embodiments described herein in any way, e.g., one, two, or three or more embodiments may be combinable in whole or in part. Further, any of the features of an embodiment of the first, second, third, fourth, or fifth, sixth, seventh or eighth aspects may be made optional to other aspects or embodiments. Any aspect or embodiment of a method can be performed by a system or apparatus of another aspect or embodiment, and any aspect or embodiment of a system can be configured to perform a method of another aspect or embodiment.

DETAILED DESCRIPTION OF EXEMPLARY EMBODIMENTS

Figure 1:
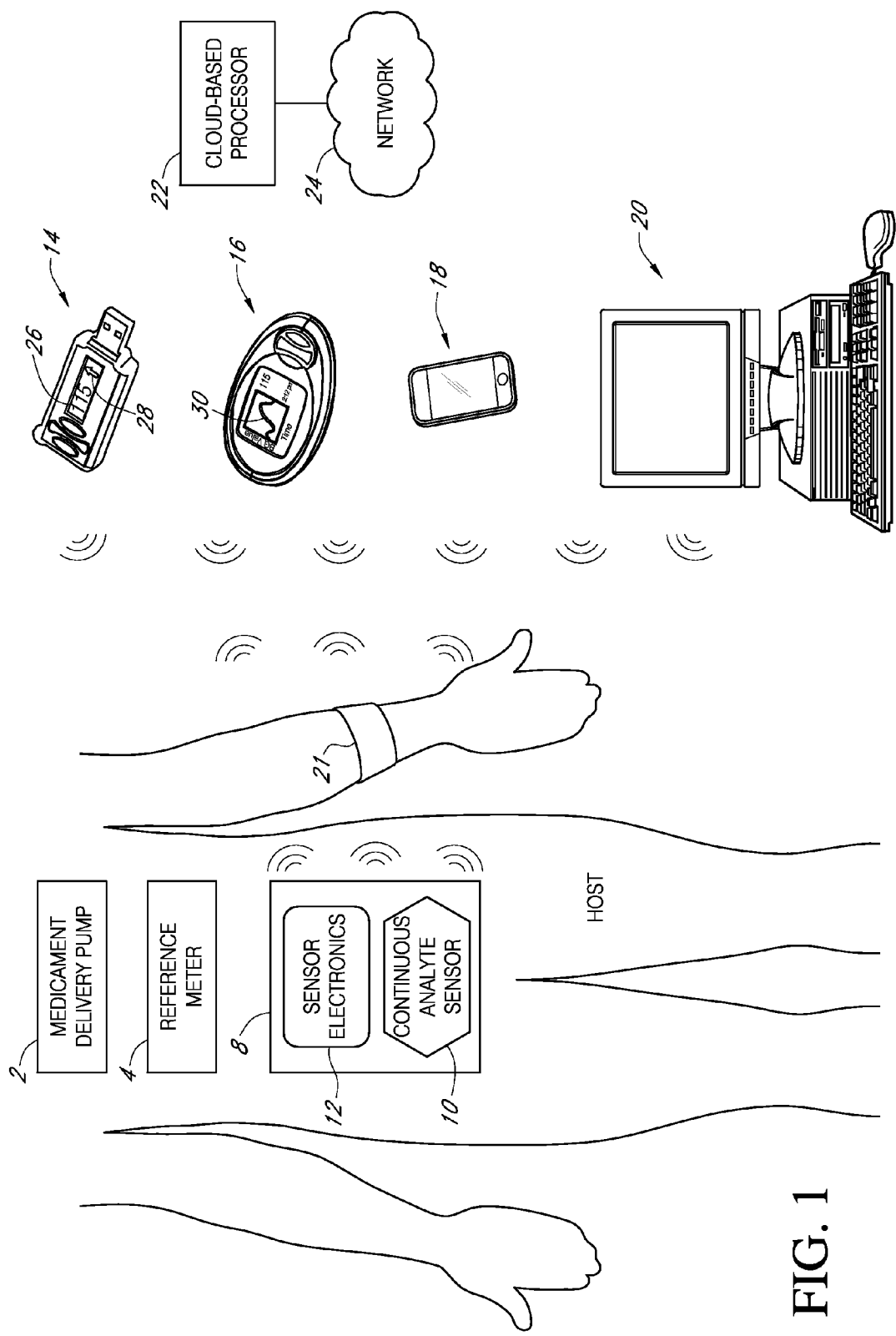
FIG. 1 is a block diagram of an integrated system of the preferred embodiments, including a continuous glucose sensor and a medicament delivery device.

Consider the specific example of continuous glucose monitoring. For diabetics, the glucose monitor can literally be the difference between life and death. Characteristics of the users of glucose monitors vary on many dimensions. Each has their own medical needs. Each user has an individual level of technical sophistication. Each user has their unique educational background, language, and cultural references. Each user participates in their own set of activities at varying degrees of intensity. Furthermore, characteristics are not static, that is, they may change over time. These are but a few factors which may influence how, when, and why a patient uses (or chooses to ignore) their glucose monitor.

One non-limiting advantage of the described features is to provide an interface which is adapted to the patient. The adaptation considers active and/or passive data associated with the patient to generate an interface suited to the patient's unique characteristics and behavior. Rather than adjusting the interface statically via preferences, dynamic tailoring of the interface can help improve the patient's experience with the monitoring device and ultimately achieve more consistent and accurate usage of the device in compliance with a prescribed treatment plan. Furthermore, the system may be configured to identify adaptations in real-time such that the system continually assesses ways in which it and/or the user may adjust to maximize the desirable outcome(s) as the data becomes available.

The following description and examples illustrate some exemplary embodiments of the disclosed invention in detail. Those of skill in the art will recognize that there are numerous variations and modifications of this invention that are encompassed by its scope. Accordingly, the description of a certain exemplary embodiment should not be deemed to limit the scope of the present invention.

To ease the understanding of the described features, continuous glucose monitoring is used as part of the explanations that follow. It will be appreciated that the adaptive systems and methods described are applicable to other continuous monitoring systems. For example, the features discussed may be used for continuous monitoring of lactate, free fatty acids, heart rate during exercise, IgG-anti gliadin, insulin, glucagon, movement tracking, fertility, caloric intake, hydration, salinity, sweat/perspiration (stress), ketones, adipanectin, troponin, perspiration, and/or body temperature. Where glucose monitoring is used as an example, one or more of these alternate examples of monitoring conditions may be substituted.

The term "continuous glucose sensor," as used herein is a broad term, and is to be given its ordinary and customary meaning to a person of ordinary skill in the art (and is not to be limited to a special or customized meaning), and generally refers to a device that continuously or continually measures the glucose concentration of a bodily fluid (e.g., blood, plasma, interstitial fluid and the like), for example, at time intervals ranging from fractions of a second up to, for example, 1, 2, or 5 minutes, or longer. It should be understood that continual or continuous glucose sensors can continually measure glucose concentration without requiring user initiation and/or interaction for each measurement, such as described with reference to U.S. Pat. No. 6,001,067, for example.

The phrase "continuous glucose sensing" or "continuous glucose monitoring" as used herein are a broad terms, and to be given their ordinary and customary meaning to a person of ordinary skill in the art (and is not to be limited to a special or customized meaning), and generally refers to the period in which monitoring of the glucose concentration of a host's bodily fluid (e.g., blood, serum, plasma, extracellular fluid, etc.) is continuously or continually performed, for example, at time intervals ranging from fractions of a second up to, for example, 1, 2, or 5 minutes, or longer. In one exemplary embodiment, the glucose concentration of a host's extracellular fluid is measured every 1, 2, 5, 10, 20, 30, 40, 50 or 60-seconds.

The term "substantially" as used herein is a broad term, and is to be given its ordinary and customary meaning to a person of ordinary skill in the art (and is not to be limited to a special or customized meaning), and generally refers to being largely but not necessarily wholly that which is specified, which may include an amount greater than 50 percent, an amount greater than 60 percent, an amount greater than 70 percent, an amount greater than 80 percent, an amount greater than 90 percent or more.

The terms "processor" and "processor module," as used herein are a broad terms, and are to be given their ordinary and customary meaning to a person of ordinary skill in the art (and are not to be limited to a special or customized meaning), and generally refers to a computer system, state machine, processor, or the like designed to perform arithmetic or logic operations using logic circuitry that responds to and processes the basic instructions that drive a computer. In some embodiments, the terms can include ROM and/or RAM associated therewith.

As used herein, the term "host" generally refers to animals (e.g., mammals such as humans) and plants. The terms "subject" and "individual" can be used interchangeably with the term "host," in certain embodiments. As used herein, the term "user" generally refers to one who utilizes information obtained from a sensor, inputs information into a sensor, or otherwise interacts with a sensor, directly or via an interface. In certain embodiments a user may be a host, e.g., an individual who utilizes data from a continuous glucose sensor for self-monitoring of glucose levels. In certain embodiments the user and the host are different, e.g., a parent who utilizes data from a continuous glucose sensor for monitoring a child's glucose levels or a healthcare worker who utilizes data from a continuous glucose sensor for selecting an insulin treatment protocol for a patient with diabetes.

Exemplary embodiments disclosed herein relate to the use of a glucose sensor that measures a concentration of glucose or a substance indicative of the concentration or presence of the analyte. In some embodiments, the glucose sensor is a continuous device, for example a subcutaneous, transdermal, transcutaneous, non-invasive, and/or intravascular (e.g., intravenous) device. In some embodiments, the device can analyze a plurality of intermittent blood samples. The glucose sensor can use any method of glucose-measurement, including enzymatic, chemical, physical, electrochemical, optical, optochemical, fluorescence-based, spectrophotometric, spectroscopic (e.g., optical absorption spectroscopy, Raman spectroscopy, etc.), polarimetric, calorimetric, iontophoretic, radiometric, and the like.

The glucose sensor can use any known detection method, including invasive, minimally invasive, and non-invasive sensing techniques, to provide a data stream indicative of the concentration of the analyte in a host. The data stream is typically a raw data signal that is used to provide a useful value of the analyte to a user, such as a patient or health care professional (e.g., doctor), who may be using the sensor.

Although much of the description and examples are drawn to a glucose sensor, the systems and methods of embodiments can be applied to any measurable analyte. In some embodiments, the analyte sensor is a glucose sensor capable of measuring the concentration of glucose in a host. Some exemplary embodiments described below utilize an implantable glucose sensor. However, it should be understood that the devices and methods described herein can be applied to any device capable of detecting a concentration of analyte and providing an output signal that represents the concentration of the analyte.

In some embodiments, the analyte sensor is an implantable glucose sensor, such as described with reference to U.S. Pat. No. 6,001,067 and U.S. Patent Publication No. US-2011-0027127-A1. In some embodiments, the analyte sensor is a transcutaneous glucose sensor, such as described with reference to U.S. Patent Publication No. US-2006-0020187-A1. In yet other embodiments, the analyte sensor is a dual electrode analyte sensor, such as described with reference to U.S. Patent Publication No. US-2009-0137887-A1. In still other embodiments, the sensor is configured to be implanted in a host vessel or extracorporeally, such as is described in U.S. Patent Publication No. US-2007-0027385-A1. The patents and publications are incorporated herein by reference in their entirety.

FIG. 1 is a block diagram of an integrated system of the preferred embodiments, including a continuous glucose sensor and a medicament delivery device. FIG. 1 shows an exemplary environment in which some embodiments described herein may be implemented. Here, an analyte monitoring system 100 includes a continuous analyte sensor system 8. Continuous analyte sensor system 8 includes a sensor electronics module 12 and a continuous analyte sensor 10. The system 100 can also include other devices and/or sensors, such as a medicament delivery pump 2 and a reference analyte meter 4, as illustrated in FIG. 1. The continuous analyte sensor 10 may be physically connected to sensor electronics module 12 and may be integral with (e.g., non-releasably attached to) or releasably attachable to the continuous analyte sensor 10. Alternatively, the continuous analyte sensor 10 may be physically separate to sensor electronics module 12, but electronically coupled via inductive coupling or the like. Further, the sensor electronics module 12, medicament delivery pump 2, and/or analyte reference meter 4 may communicate with one or more additional devices, such as any or all of display devices 14, 16, 18 and 20.

The system 100 of FIG. 1 also includes a cloud-based processor 22 configured to analyze analyte data, medicament delivery data and/or other patient related data provided over network 24 directly or indirectly from one or more of sensor system 8, medicament delivery pump 2, reference analyte meter 4, and display devices 14, 16, 18, 20. Based on the received data, the processor 22 can further process the data, generate reports providing statistic based on the processed data, trigger notifications to electronic devices associated with the host or caretaker of the host, or provide processed information to any of the other devices of FIG. 1. In some exemplary implementations, the cloud-based processor 22 comprises one or more servers. If the cloud-based processor 22 comprises multiple servers, the servers can be either geographically local or separate from one another. The network 24 can include any wired and wireless communication medium to transmit data, including WiFi networks, cellular networks, the Internet and any combinations thereof.

It should be understood that although the example implementation described with respect to FIG. 1 refers to analyte data being received by processor 22, other types of data processed and raw data may be received as is described in further detail herein.

In some exemplary implementations, the sensor electronics module 12 may include electronic circuitry associated with measuring and processing data generated by the continuous analyte sensor 10. This generated continuous analyte sensor data may also include algorithms, which can be used to process and calibrate the continuous analyte sensor data, although these algorithms may be provided in other ways as well. The sensor electronics module 12 may include hardware, firmware, software, or a combination thereof to provide measurement of levels of the analyte via a continuous analyte sensor, such as a continuous glucose sensor.

The sensor electronics module 12 may, as noted, couple (e.g., wirelessly and the like) with one or more devices, such as any or all of display devices 14, 16, 18, and 20. The display devices 14, 16, 18, and/or 20 may be configured for processing and presenting information, such sensor information transmitted by the sensor electronics module 12 for display at the display device. The display devices 14, 16, 18, and 20 can also trigger alarms based on the analyte sensor data.

In FIG. 1, display device 14 is a key fob-like display device, display device 16 is a hand-held application-specific computing device 16 (e.g., the DexCom G4® Platinum receiver commercially available from DexCom, Inc.), display device 18 is a general purpose smart phone or tablet computing device 20 (e.g., an Apple® iPhone®, iPad®, or iPod touch® commercially available from Apple, Inc.), and display device 20 is a computer workstation 20. In some exemplary implementations, the relatively small, key fob-like display device 14 may be a computing device embodied in a wrist watch, a belt, a necklace, a pendent, a piece of jewelry, an adhesive patch, a pager, a key fob, a plastic card (e.g., credit card), an identification (ID) card, and/or the like. This small display device 14 may include a relatively small display (e.g., smaller than the display device 18) and may be configured to display a limited set of displayable sensor information, such as a numerical value 26 and an arrow 28. Some systems may also include a wearable device 21, such as described in U.S. Patent Application No. 61/896,597 filed Oct. 28, 2103, and entitled "Devices Used in Connection with Continuous Analyte Monitoring that Provide the User with One or More Notifications, and Related Methods," the entire disclosure of which is hereby expressly incorporated by reference. The wearable device 21 may include any device(s) that is/are worn on, or integrated into, a user's vision, clothes, and/or bodies. Example devices include wearable devices, anklets, glasses, rings, necklaces, arm bands, pendants, belt clips, hair clips/ties, pins, cufflinks, tattoos, stickers, socks, sleeves, gloves, garments (e.g. shirts, pants, underwear, bra, etc.), "clothing jewelry" such as zipper pulls, buttons, watches, shoes, contact lenses, subcutaneous implants, cochlear implants, shoe inserts, braces (mouth), braces (body), medical wrappings, sports bands (wrist band, headband), hats, bandages, hair weaves, nail polish, artificial joints/body parts, orthopedic pins/devices, implantable cardiac or neurological devices, etc. The small display device 14 and/or the wearable device 21 may include a relatively small display (e.g., smaller than the display device 18) and may be configured to display graphical and/or numerical representations of sensor information, such as a numerical value 26 and/or an arrow 28. In contrast, display devices 16, 18 and 20 can be larger display devices that can be capable of displaying a larger set of displayable information, such as a trend graph 30 depicted on the hand-held receiver 16 in addition to other information such as a numerical value and arrow.

It is understood that any other user equipment (e.g., computing devices) configured to at least present information (e.g., a medicament delivery information, discrete self-monitoring analyte readings, heart rate monitor, caloric intake monitor, and the like) can be used in addition or instead of those discussed with reference to FIG. 1.

In some exemplary implementations of FIG. 1, the continuous analyte sensor 10 comprises a sensor for detecting and/or measuring analytes, and the continuous analyte sensor 10 may be configured to continuously detect and/or measure analytes as a non-invasive device, a subcutaneous device, a transdermal device, and/or an intravascular device. In some exemplary implementations, the continuous analyte sensor 10 may analyze a plurality of intermittent blood samples, although other analytes may be used as well.

In some exemplary implementations of FIG. 1, the continuous analyte sensor 10 may comprise a glucose sensor configured to measure glucose in the blood using one or more measurement techniques, such as enzymatic, chemical, physical, electrochemical, fluorescent, spectrophotometric, polarimetric, calorimetric, iontophoretic, radiometric, immunochemical, and the like. In implementations in which the continuous analyte sensor 10 includes a glucose sensor, the glucose sensor may be comprise any device capable of measuring the concentration of glucose and may use a variety of techniques to measure glucose including invasive, minimally invasive, and non-invasive sensing techniques (e.g., fluorescent monitoring), to provide a data, such as a data stream, indicative of the concentration of glucose in a host. The data stream may be raw data signal, which is converted into a calibrated and/or filtered data stream used to provide a value of glucose to a host, such as a user, a patient, or a caretaker (e.g., a parent, a relative, a guardian, a teacher, a doctor, a nurse, or any other individual that has an interest in the wellbeing of the host). Moreover, the continuous analyte sensor 10 may be implanted as at least one of the following types of sensors: an implantable glucose sensor, a transcutaneous glucose sensor, implanted in a host vessel or extracorporeally, a subcutaneous sensor, a refillable subcutaneous sensor, an intravascular sensor.

In some implementations of FIG. 1, the continuous analyte sensor system 8 includes a DexCom G4® Platinum glucose sensor and transmitter commercially available from DexCom, Inc., for continuously monitoring a host's glucose levels.

Figure 2:
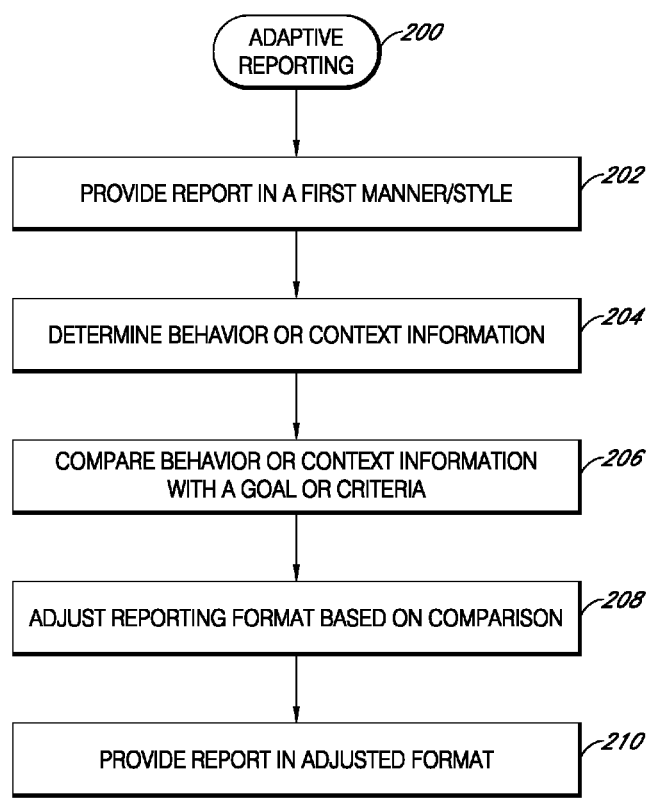
FIG. 2 is a process flow diagram of a method of adjusting an interface format/style of physiological information based on behavioral and/or contextual information.

FIG. 2 is a process flow diagram of a method of adjusting an interface format/style (e.g., graph, display of sensor data, buttons, alarms, default screens, and preferences for interaction) of physiological information based on behavioral and/or contextual information. The adaptive reporting process 200 shown in FIG. 2 recognizes a pattern based on one or more inputs that can adaptively trigger support/partner mode. Recognizing the context of the patient, the adaptive reporting process 200 may cause the device to switch into a context appropriate mode of operation. The context appropriate mode may be adapted to determine how long, how much content (e.g., alert, alarm, screen, information, etc.) to present via an output of the device, how much content was ignored, daily reset, thereby subtly taking over without effort from the user. In some implementations, the adaptation may be based on a pre-set goal such as a target glucose reading.

The process of providing automatic adaptation of a user interface feature (e.g., settings or functions) based on behavioral and/or contextual information solves a long felt need of personalizing general purpose devices for healthcare use, or health care devices intended for use with a wide variety of user preferences, in a simple and intuitive manner. That is, not all users have the same preferences when it comes to personalization of interface format/style of physiological information of a medical device (e.g., user interface settings or functions for health care data), especially a consumer-driven medical device. Some users may be tech savvy and enjoy reviewing large amounts of their health data; other users may prefer a simpler interaction. Many users fall in between and their preferences may be influenced by the context surrounding their interaction. Unfortunately, creating devices that are highly customizable also tend to be highly complex, and vice versa, therefore do not address the full spectrum of users. There remains a need for automatically and adaptively understanding the behavior and context of the user of a consumer-driven medical device that is highly intelligent and allows for adaptation of the user interface. In one implementation, these needs are met by providing a report in a first matter/style (202); determining behavior or contextual information (204); comparing the behavior or contextual information with a goal or criteria (206); adjusting the reporting format based on the comparison (208) and providing a report in the adjusted format (210), a device may be efficiently, intuitively and intelligently personalized for optimizing health care management and use, without requiring a complex or comprehensive understanding of technology, human behavior (or context) and health data that would otherwise extremely difficult, inefficient and likely impossible for a human to perform as is made possible by the systems and methods described herein.

"Adaptive reporting" generally refers to the process, quality, or act of updating or changing the reporting style or format (e.g., of a human detectable interface associated with the medical device or its data) based on received information such that a functional feature is adjusted. In some implementations, the adaptation is based on predictive inferences drawn from the information collected for the associated user. An adaptive reporting system or method may be contrasted with a reactive (or dynamic) reporting system or method. Whereas a reactive or dynamic reporting system or method may provide a single reactive adjustment in real time based on a single event or selection (e.g., in reaction to a stimulus), an adaptive reporting system or method anticipates the event based on the previous behavioral or contextual patterns identified for the user over time and makes an ongoing adjustment to a setting or functionality based thereon. One non-limiting benefit of adaptive reporting systems and methods in accordance with some implementations is to avoid the occurrence of an undesirable event altogether by adjusting the system in anticipation of the negative event.

The adaptive reporting process 200 shown in FIG. 2 may be implemented in whole or in part using a continuous monitoring system such as the devices shown and described in FIG. 1. The adaptive reporting process 200 may be implemented in hardware such as via a field programmable gate array or application specific integrated circuit or a microcontroller specifically configured to implement one or more aspect of the adaptive reporting process 200 described in relation to FIG. 2. In general, the reporting may be provided (displayed) via a user interface (e.g., human detectable interface), such as a continuous monitoring device, a patient record system, a smartphone, or a social media internet site.

For ease of explanation, FIG. 2 will be described with reference to glucose monitoring. The adaptive reporting process 200 begins at block 202 where glucose information is reported to user/patient in a first manner or style. Not all users/patients intuitively prefer, or are able to cognitively handle, a common reporting style. Furthermore, not all users/patients may be situated to receive the same report at all times. For example, a younger patient who regularly interacts with electronic devices may adapt differently to the continuous monitoring system than an older patient who rarely interacts with electronic devices. As another example, if a user/patient is driving, it may be desirable to provide a concise report of information that can be comprehended while operating a car. Similarly, if the user/patient is at home watching television, a more robust report may be desirable. Such variations may affect patient behavior and impact utilization of the device and/or outcomes from using the device.

In some implementations, the first manner or style may be predetermined such as during device manufacture time. The first manner or style may be selected so as to provide the basic information. In some implementations, a learning phase may be selected for the device. During the learning phase, the device may utilize a default first manner or style. In some learning phases, it may be desirable to avoid reporting or to provide a limited report on some interactions/events until after expiration of the learning phase. The duration of the learning phase may be based on the quantity of input information before deciding to turn on (or prompt) a feature at all. For example, a new device may not have information regarding the patient. The learning phase may receive information about the patient such as physiological readings from the glucose sensor, activity information (e.g., pedometer information), location information (e.g., GPS coordinates), and the like. Once sufficient data to begin the adaptation process is obtained, the learning phase may terminate.

A style or manner of reporting may include audio feedback characteristics such as frequency, tone, and volume of an alarm. The style or manner of reporting may include visual characteristics such as resolution of a trend graph, brightness intensity, colors for graphs, interface iconography, interface symbology (e.g., for alerts), magnification level of displayed information, and the like. The style or manner of reporting may include information display characteristics such as the orientation of trend graphs, trend graph ranges, graph color scheme, dynamic trend graphs, and the like. The style or manner of reporting may include a reporting frequency, a number of alerts of a particular type (e.g., actionable alerts, informational alerts, etc.), an amount of avatar help (e.g., quantity of interactive automated assistance via an animated character display), a vibration intensity and/or frequency, amount of data to display (e.g., past hour, 2 hours, etc.).

Other reporting related styles or manners that may be provided (and adapted over time) include a default display for the report, levels of discretion for reporting based on context, input configuration for a report (e.g., hitting a key on the device while viewing a trend graph temporarily magnifies trend graph to trend line range or to magnify around current glucose level/trend), glucose acceleration information (e.g., your glucose speed is still going up, but not as quickly—a sign that insulin is starting to act), prediction mode time, future mode time/inputs (e.g., based on glucose, insulin, exercise, and other input information that may be available, a prediction of future mode time or inputs may be generated. In some implementations, the prediction may be based on previous user data whereby similar past patterns of inputs can be used to improve estimate).

Alert and/or alarm settings that may be provided (and adapted over time) include one of multiple high level contextual categories in some implementations. For instance, there could be three categories: information only, safety mode, and attentive mode. In the information only configuration, the system turns off all alarms and alerts and only displays the information. In safety mode, the system sets alarms at severe hypo and hyperglycemia. In attentive mode, the system is configured to operate under tighter glycemic control goals (i.e., 80 to 150 mg/dl). These settings would be the defaults but the system may, over time, adapt each individual setting (e.g., alert level, volume, etc.). The modes may also be applied selectively by the system based on context. For example, while in a meeting at work, the information only mode may be desirable.

The style and/or manner may include order of screens or menu items or hide items, which may be adapted over time. The style or manner may also include a frequency and/or content of any information published to other devices or to other people such as a doctor or caregivers, which may also be adapted over time.

Figure 4:
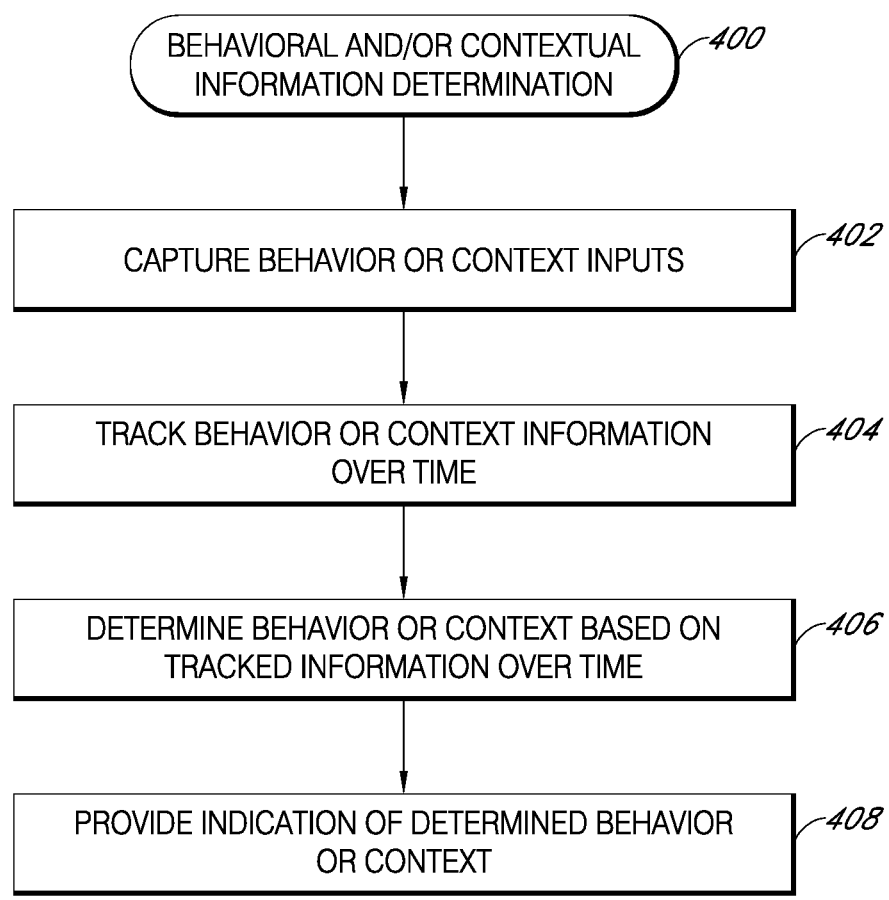
FIG. 4 is a process flow diagram of a method of determining behavioral and/or contextual information for a patient.

At block 204, as shown in FIG. 2, behavioral and/or contextual information about the user/patient is determined. FIG. 4 provides more detail on how behavior and/or contextual inputs may be captured, tracked, determined and indicated, any of which may be applied as a subroutine at block 204 of the adaptive reporting process 200. By identifying certain contexts or behaviors during natural use of the device, the system can adapt the reporting style for the context or behavior of that user. For example, the system may identify when a patient is frustrated or confused by detecting the patient staring at the screen for a long period of time via eyeball tracking or other image or haptic based detection. As another example, the patient may be identified as satisfied based on facial pattern recognition information obtained from image data. As a further example, the system may determine the patient is in a certain social situation such as in a work meeting or out to dinner with friends based on GPS and/or calendar information. As yet another example, the system may determine the patient is exercising or driving via input from an accelerometer, calendar, and/or GPS). In each of these examples, the context and behavior can be associated with the physiological information without actually requiring the user to input the determined information.

Context and behavior information can also be obtained via user input. For example the user may be prompted to indirectly guide or adjust the behavior of the system by asking them to answer weighted questions. For example, "On a scale of 1 to 5, do you prefer people knowing everything about you", "How often do you check your friends Facebook pages", "How often do you check the time or temperature". Each question can be related to one or more underlying reporting style or manner. For example, the questions regarding knowing everything or Facebook may be used to establish a frequency and quantity of data to report to others.

While some implementations may achieve a more accurate adaptation using indirect questions, in some implementations the system may be configured to directly receive weighted preferences for various reporting styles or manners. For example, a slider interface control may be calibrated from "very little" to "as much as possible" for a "how much feedback do you want", "how much information do you want to share with friends or doctor", etc. These direct questions can impact how often, if at all, a specific alarm is triggered. Note, however, the user/patient is not directly asked whether to turn off the alarm in this implementation.

Determination of behavioral and/or contextual information about the user/patient will be discussed in further detail below, such as in reference to FIG. 4. Namely, contextual and or behavioral inputs may be captured as described at block 402; the behavior and/or contextual inputs may be tracked over time to collect a database of information as described at block 404; and the inputs may be processed to determine behavioral and/or contextual information about the patient as described at block 406, based on which an indication of the contextual and/or behavioral information may be optionally provide as described at optional block 408 and/or the contextual and/or behavioral information directly inputted to block 204 described herein.

At block 206, the behavioral and/or contextual information is compared to a goal/criterion. The goal/criteria may be an adaptive goal or a predetermined goal as will be described in further detail in FIG. 5 (see, e.g., block 502 and 510). Sometimes a patient's behavior and/or context will limit their ability to gain full benefit from the physiological information, by setting goals that take into account behavior and/or context, the useful physiological information can be individualized to meet a user's needs without any effort on their part.

Exemplary goals include an amount of: interaction with the device, amount of time in target, amount of time outside of target, device location (e.g., not leaving device behind), data retention, calibrating frequency, standard deviation, pattern management (e.g., times of day in/out of target), time spent on certain screens, time spent hypo, time spent hyper, time spent at high rates of change, and time spent at low rates of change. Criteria may be set to determine whether the user has met the goals, for example, criteria may interaction with the monitoring system at least 10 times per day, at least 22 hours per day within target, no more than 2 hours per day outside of target, amount of data captured, number of fingersticks entered, number of menu selections and/or button clicks, etc. In general, it should be understood that goals may be used to define by criteria (both of which may be adaptively modified over time as described with respect to FIGS. 5 and 6), which may be compared with behavioral and/or contextual information determined at block 204.

In some exemplary embodiments GPS input information may be used by the system to determine a user went for a walk in the hills, which may be compared with a goal/ criterion. Input information from an accelerometer may be used by the system to determine they exercised more or they slept more, which may be compared with a goal/criterion. Input from the Internet of Things (IOT) (e.g., machine to machine communication) may be used by the system to determine if the user watched less TV or bought more healthy food for the refrigerator, which may be compared with a goal/criterion. Blood pressure data obtained from a blood pressure sensor, input manually, or retrieved from memory (e.g., patient care record) can be used to acknowledge the associated user managed stress better, which may be compared with a goal/criterion. Goals will be described in further detail with reference to FIG. 5.

The incorporation of machine to machine communication provides several non-limiting advantages to the effective treatment of a patient with a continuously monitored condition, wherein data obtained from machine to machine communication may be compared to goals/criterion. The device can communicate with other networked devices thereby expanding the type of data which may be provided to the system and collected. For example, the monitoring device may be in data communication with various devices in the patient's home such as a television, refrigerator, temperature control system, computer, gaming console, security system, and the like. The monitoring device may be configured to automatically discover the closest networked devices that can provide data (wherein the goal/criteria is based on nearness and the context information includes nearby devices, including their location/nearness). In some implementations, the monitoring device may be configured to connect with a pre-determined set of devices. In such implementations, additional security credentials may be provided to control access to the data. As two examples, the data communication may be via a central network (e.g., local area home network) or via a peer-to-peer mesh network.

Consider the following implementation including machine to machine context information. The networked sensor (e.g., a GPS capable device) can provide input to the system for determining when the user of the monitoring device is at home (i.e., context information). The GPS may be a standalone navigation unit, included in the monitoring device, or included in another device configured to provide the location information such as a smartphone. Once at home, the light bulbs may be connected to the network (i.e., criteria for using light bulbs includes GPS location indicating the patient is home). The light bulbs may be used to provide reports to the user while at home. For example, a report may include transmitting a signal to the light bulb to change color when the user is high or low at home (e.g., turns purple for high and orange for low). If the system received inputs which indicate that the user's analyte level is below a threshold and is not acknowledging alarms, via the Internet of Things (IOT), a hierarchy of alarms can be transmitted. First, text messages are sent to pre-determined followers that are nearby (known by their GPS locations). Followers may be notified based on their proximity to the person (e.g., no need to notify a person who is determined to be located in different state). The front door lock opens so nearby followers can get into users house (see, for example, Lockitron a networked door lock manufactured by Apigy Inc.). If nearby followers are not available, an email or text message may be issued to emergency services. Front door light (also networked) can change to pink, allowing emergency services to quickly identify which house they need to look for.

Followers may include all members of a community of users. For example, a follower network of all DexCom users can be created whereby each user is identified as a follower of another person in the DexCom network who is nearby. In this way, strangers can help strangers if nearby. Such a social system can assign points for helping strangers out and may attain an elevated status in the diabetes community. These interactions can further facilitate awareness and help save lives. The follower network may be configured based on privacy preferences or other reporting criteria (e.g., forms of reporting to use via the network, amount of data to transmit, etc.).

As described thus far, the monitoring device provides messages to the devices via the machine to machine communication. In some implementations, communication may occur in the reverse direction, such as a severe low glucose with no signs of movement may activate a phone speaker which permits playback of sound (e.g., a phone call) via the monitoring device to anyone nearby who might be able to help.

At block 208, the manner, in which the information derived from the continuous monitor is reported, is adjusted. The adjustment may be based on the comparison of block 206. For example, improvements in user interaction/displays/alarms, etc. could be identified by the system. Such identification may be preemptive and adaptive based on patterns. Some exemplary reporting manners and styles that may be adjusted are described with referenced to block 202, however, it should be understood that any manner or style (characteristic or feature) of reporting information may be adjusted in any way as is appreciated by one skilled in the art. The amount of iterative and/or total adjustment of reporting styles may be limited by boundaries predefined by the manufacturer and/or set by a user (based on human factors studies, for example). By iteratively trying new reporting styles and watching how the user's behavior responds or their ability to respond (e.g., would not respond when in a certain context, such as a meeting) and/or contextually applies differently, the reporting style can be individualized for a patient and adapted over time as a change with the changing environment, behavior, and/or context of the patient. The adjustment in some implementation is performed automatically. In some implementations, the adjustment may be performed via a recommendation whereby one or more possible adjustments are provided and an indication of one or more adjustments to apply is received.

The adjustment to the style or manner of reporting may include audio feedback characteristics such as changing frequency, tone, and volume of an alarm (e.g., increasing, decreasing or other changes). The adjustment to the style or manner of reporting may include changing visual characteristics such as resolution of a trend graph, brightness intensity, colors for graphs, interface iconography, interface symbology (e.g., for alerts), magnification level of displayed information, and the like. The adjustment to the style or manner of reporting may include changing information display characteristics such as the orientation of trend graphs, trend graph ranges, graph color scheme, dynamic trend graphs, and the like. The adjustment to the style or manner of reporting may include changing a reporting frequency, a number of alerts of a particular type (e.g., actionable alerts, informational alerts, etc.), an amount or type of avatar help (e.g., quantity of interactive automated assistance via an animated character display), a vibration intensity and/or frequency, amount of data to display (e.g., past hour, 2 hours, etc.). The adjustment to the style or manner that may include a default display for the report, a level of discretion for reporting based on context, an input configuration for a report (e.g., hitting a key on the device while viewing a trend graph temporarily magnifies trend graph to trend line range or to magnify around current glucose level/trend), glucose acceleration information (e.g., your glucose speed is still going up, but not as quickly—a sign that insulin is starting to act), a prediction mode time (e.g., longer or shorter prediction horizon), a future mode time/input (e.g., based on glucose, insulin, exercise, and other input information that may be available, a prediction of future mode time or inputs may be generated. In some implementations, the prediction may be based on previous user data whereby similar past patterns of inputs can be used to improve estimate). Alert and/or alarm settings may be adjusted, such as one of multiple high level contextual categories, wherein the system may, over time, adjust the high level contextual categories and/or adapt each individual category setting (e.g., alert level, volume, etc.). The modes may also be applied selectively by the system based on context. For example, while in a meeting at work, the information only mode may be desirable. As another example, the style and/or manner adjustment may include reorder of screens or menu items or hide items. The adjustment to the style or manner may also include changing a frequency and/or content of any information published to other devices or to other people such as a doctor or caregivers, which may also be adapted over time.

As another example adjustment, the received information may indicate that a response is not received at night unless the alarm is provided at a certain volume. In this situation, the patient may be a deep sleeper and the default alarm volume during periods of sleep needs to be louder. As another example, the patient's spouse may be identified as a light sleeper (context) so alarms should be vibration only (adjustment) until a certain glucose reading (e.g., LOW 55) is hit. As another context adaptation, or when the patient is identified as going for a walk (behavior/context), the device may determine that a user wants a "diabetes vacation" for just 30 minutes and does not want to be bothered unless LOW 55 may be hit within the hour (adaptation). Environmental adjustments may also be provided such as if the user is determined to be outside most of the time (context) a brighter contrast may be used for a trend screen display. Other adjustments can include providing higher level of discretion (adjustment) when detecting the location a work meeting (context), providing a basic, high-level report to a user determined to be overwhelmed with data or to a newly diagnosed user. In some implementations, the adjustments may feature a graduation scheme whereby upon completion of certain criteria, the reporting style is adapted to a next-level of sophistication. The adjustments may provide a set of adaptations that are continuously applied (once adjusted, until the next adjustment) and/or that are applied depending on the behavior or context identified at any particular time (a profile of adjustments that depend on real-time context/behavior).

A further example of an adjustment includes altering the iconography and/or alert symbols that reflect real time data. For example, when a low alarm goes off, the icon on the device for "low alarm" could show an image of the trend graph going low with actual data points from glucose readings instead of a generic representation of a low glucose chart.

Organizing the adapted reporting may include identifying a hierarchy of reporting beginning with basic reporting and escalating to a more critical/complex report. For example, in the case of the deep sleeping patient, sensor inputs may indicate that the user is not acknowledging low glucose alarms triggered during the night. In a diabetic situation, this can be caused by the person sleeping or, more critically, that the person has entered a dangerously low state and is unresponsive. The reporting may be adapted to provide an initial loud alarm during evening hours and progressively increase volume over a period of time. The hierarchy may also include a threshold point whereby alternate reporting means are used to provide the alert such as a phone call to the user's home, a phone call to neighbor, and, perhaps the ultimate alert being defined as a phone call to emergency services (e.g., 911).

Based at least in part on the collected context and behavior information in conjunction with the monitored physiological characteristics, the system is configured to assess how a patient's condition behaves and responds over time. For example, the weather (context) combined with a patient's exercise regime (behavior) could cause glucose lows. The patient may not identify this correlation, but through analysis of the collected information, a prediction that the low may occur based on the past events. In such implementations, the monitor may take proactive steps to maintain the patient's levels such as administering medication, increasing the frequency of monitoring, displaying a warning message, or the like.

Analysis of the specific characteristics of the patient's condition can be useful in identifying other trends or anomalies with the specific patient. For example, if atypical patterns are detected, other issues may be assessed as potential causes of the variations. Such issues may include food allergies, celiac disease, gastroparesis, etc., which may be identified based on the context/behavior information. This past knowledge informs guidance/advice to best respond to certain situations or trends. For example, a potentially rebound hypo may be detected as occurring on a regular basis. The system can be adapted to automatically alert the patient at a time they should eat to best avoid both hypo(glycemia) and a rebound hyper(glycemia). Trends may also be classified in the moment based on hypo/hyper risk, rebound, etc. and frequency of reporting adapted accordingly as risk of a glucose excursion changes.

The changes to reporting characteristic need not be in the same category as the behavioral information. For example, while increased user interaction could trigger a change in the interface, increased hypoglycemia could also trigger a change in the interface. In some implementations, one type of behavioral information can be used to adjust multiple reporting characteristics. Similarly, multiple elements of behavioral information may be used to adjust a single reporting characteristic.

The context/behavior information may be used to configure general device features. For example, the general device user interface may be reconfigured, graph, display of sensor data, buttons, alarms, default screens, and preferences for interaction. In some implementations, it may be desirable to interact with the user via a game. In such a mode, rewards may be provided when desired behaviors are detected. In such implementations, the type of rewards which are provided, amount of reward, and frequency of rewards given may be adjusted based on the context/behavior information.

Discretion may be desired for certain users. As one way to ensure discretion, first level alarms may be provided which only vibrate without turning on the screen or otherwise "awaken" monitoring device features. In such implementations, the monitoring device may awaken when a button press is detected. The button press may include a defined series of buttons which permit inadvertent awakening through, for example, a "pocket push." This may further provide a level of security to the device by allowing a custom awake input to be identified for the monitoring device.

At block 210, the report is provided based on the identified adjustments. As discussed, altering the reporting of glucose information based on personalized interaction can help increase usage, response to provided information and alerts, and ultimately improve outcomes (e.g., health). The user's behavior and/or context can continue to be tracked and their response determined. Additional adjustments may be identified through subsequent iterations of the adaptive reporting process 200. The adjustments to the reporting format and/or goals/criteria are used for adapting the reporting format so that interaction with the physiological information is personalized for a particular person, in a particular situation, at a particular time.

How the report is provided is a further adaptation which may be performed by the system based on the obtained contextual and/or behavioral information. For example, a report may be intended for another device (e.g., machine to machine device), or for human consumption (e.g., email, text information). Example report destinations include an insulin pump, a networked storage device (e.g., cloud storage), a social media community, a Smart TV, a computer or an application running on a computer (e.g., widget), a phone, a watch, doctors or other care providers, to PCS (patient customer support) team, parent, loved one, a follower (e.g., a person with whom a continuous glucose monitoring (CGM) patient is "sharing" their CGM data), an activity tracker, a cell phone, a ring, a pendant, smart refrigerator, a medical system like hospital equipment or hospital network, gaming or applications on phone where rewards are included as game points/currency (e.g., credits that may be used in-game to acquire additional features), and the like.

Providing the report at block 210 may include providing positive feedback to the user. A determination of how the patient responds to the positive feedback (e.g., more success with positive feedback as compared to less or no positive feedback) could be tracked as a patient input for context/behavior information. The system may be configured to use this information to adapt goals and/or further resulting reporting formats such as described with reference to block 208. The feedback may be organized at an individual patient level. The feedback may be provided to a group or team of users so that the incentive is relationship or team-based/connection or partnering with others.

Devices which include such feedback can improve confidence in diabetics by positive reinforcement. Providing the report at block 210 may include identifying positive trends or behaviors and providing this information in a report. For example, simple goals may be associated with a user, such as to wear the sensor for two days or to check their monitored number five times in a day. Such simple goals may be organized into a hierarchy such that easier goals must be accomplished first before "graduating" to next level of complexity.

The system may identify a pattern of positive events, such as an improvement or a good monitoring report, and provide a reward. The reward may be known by the patient a priori or be a surprise reward. The reward may include a "bragging" reward tied to social media such as a limited access avatar, icon, or the like.

Providing the report may further include indication of goals and achievement thereof. Goals can be user defined (e.g., by patient, doctor, parent) or predetermined (e.g., library of goals for diabetes patient). User gets rewards and badges for achieving these goals. Via badges, user advances through the ranks of CGM knowledge, and moves to the next step, thus reinforcing success. The information collected regarding goal achievement may provide data as to which interventions are more effective than others.

Other examples of feedback which may be provided at block 210 include acknowledgement of a period of time when the system does not detect a target analyte level below a threshold. Such periods of time may be referred to as "no hitter days." Other example forms of feedback are praise for going to a doctor appointment, or scheduling of other appointments to help manage the full picture of living with diabetes (e.g., eye doctor, dentist, etc.). On a day when the glucose control did not meet the target criteria/threshold feedback may be provided to encourage or motivate the patient. Such days may be referred to as "bad" days. The target criteria or threshold for "no hitter days" or "bad days" may be preset, default, user defined, or adapted over time). An example of feedback for a "bad" day may include selection by the system of a message which offers hope (e.g., it's ok, everyone has an off day). In some implementations, the message may include patient specific information such as, "Remember X day when you had a no hitter? Tomorrow is a new day with a fresh start, get some rest and try again!" In this way, the patient can be reminded that not all experiences with diabetes are positive, but regardless of hard efforts you have to wake up and do the same thing with the same constant effort all over again so it's important to improve confidence by acknowledging that "bad" days happen but there will be/can be good days ahead.

Based on the initial processing, additional information or inputs may be identified as being useful to further adaptation. For example, if no location information was identified during the adaptive reporting process 200, at block 210, a request to enable the GPS or provide a GPS input may be included. For inputs which were received, configuration of the sensors providing the inputs may be assessed and recommended changes may be suggested. For example, the sensor insertion location can affect the monitoring process. Upon identifying variance in the data received from the inserted sensors, adjustments to the sensors may be suggested.

As one example implementation, after providing the report (block 202), the system determines the user has not calibrated the device in several days. This determination is based on received data from the device which is stored each time the device is calibrated. The date of the last calibration may be stored in a memory and compared to the current date (to determine behavioral information at block 204). If the number of days exceeds a threshold, the absence of calibration may be identified (by comparing behavior information to goal/criteria at block 206). As the accuracy of the report may be affected by the calibration, upon identifying this behavior, the system may adapt the report to include feedback or other content (at block 208). The feedback may be identified from a catalog of feedback items categorized by behavior and/or context. The system may identify a static item (e.g., textual message regarding the importance of calibration) for inclusion within the report. The system may identify a dynamic item. The dynamic item may include user specific information such as the number of days since last calibration. The dynamically included information may be selected based on the received behavior and/or contextual information for the user. The system may identify an interactive item. An interactive item is one which includes a prompt for the user to provide a response. The response may be free-form (e.g., open ended question with text information provided in response), or limited form (e.g., multiple choice, sliding scale, validated values). Once included in the report (at block 210), the feedback may be presented within the report or via a messaging interface included within the device (e.g., notification icon, text message, email). If the feedback includes an interactive item, the device receives the user input and transmits the response to the system for further processing. The further processing may include storing the response, natural language extraction of keywords from the response, identifying a subsequent feedback item, and the like.

Having described a method of adjusting an interface format/style for physiological information based on behavioral and/or contextual information in FIG. 2, certain example embodiments incorporating the features described may serve to further highlight the innovative aspects of the method.

In another example, the monitor reports CGM data to user with high sensitivity alarms (at block 202). The system determines that the user shows a pattern of ignoring alarms (behavior determined at block 204). The determination is based on an analysis of frequency of interaction with the CGM display and alarm state lasting greater than 1 hour on average. The system may identify a goal for this user from a library of pre-determined goals based on the identified behavior pattern or contextual information. The goal may be to experience alarm states lasting no more than an hour on average (pattern) and/or interaction with the device at least twice during an alarm state lasting more than an hour (block 206). To help achieve this goal, the system may further identify adaptations to the reporting style such as changing tone, increasing volume and/or increasing frequency of alarms (block 208). With the adapted alarming format, the user continues using the monitor without necessarily having to perform the analysis and adjustment identified by the system (block 210). In some implementations, the adaptation may be confirmed through a received user input (e.g., active a control acknowledging the change).

Further details about alarms such as setting alarms, alarm states, criteria for alarms may be found in U.S. patent application Ser. No. 13/742,694 filed January 16, and entitled "Systems and Methods for Providing Sensitive and Specific Alarms," the entire disclosure of which is hereby expressly incorporated by reference. The alarms, states, and/or criteria described may be adapted using the systems and methods discussed herein.

In another example, the monitor provides personalized assistance in maintaining analyte levels within a target range. The system recognizes that the user only uses a certain interface of the system (after reporting at block 202, behavior is determined based on screen views at block 204 and compared to a criterion at block 206). The system automatically adapts the menu/screen prioritization to a predetermined scheme associated with users under good glucose control (e.g., average reading over a period of time within a threshold amount) at block 208. The adaptation (208) may include storing a flag indicating the particular menu item is to be hidden (210). The adaptation (208) may include adjusting a list of menu items used to generate the display such that the adjusted list features the items more frequently used near the top of the list and less frequently used items lower in the list (210). If the user is not under good glucose control the system may be adapted (at 208) to provide (at 21) tips on other interfaces which may be used to increase control. The tips may include information messages, advertisements for other products, or additional behavioral/contextual inputs which may be useful to incorporate into the monitoring system.

Where advice/guidance is provided, the provided information may be based on known best practices to correct/avoid devolving trend or riskier glucose excursion. The information can be selected and/or reference past data of user or similar population as well. The provided information can include multimedia information, textual information, or audio information. The information may be stored in a database and associated with one or more context, behavior, or monitored conditions.

In some exemplary implementations, the system may determine the behavior (at 204) that a patient is not calibrating at suggested intervals (e.g., every 12 hours) at 206. In some cases, it may be determined that the patient is skipping calibrations completely. To decrease the amount of time CGM is prompting for calibrations, the reporting for this user is adapted (at 208) to provide a message after certain number of missed calibrations that monitored values may not be accurate due to system being out of calibration.

In some exemplary implementations, the system may determine that the patient does not set a high alert or low alert. One of the advantages of continuous monitoring is to have the patient make changes to their behavior in light of past trends. For such a patient, the monitor can determine if person is spending too much time in high or low ranges. The monitor may then be adapted to provide a report (e.g., once every 3-4 days) letting the patient know that blood glucose is extremely high (e.g., 400 mg/dL) or running on the low side (e.g., 60 mg/dL) at certain times of the day. This is just one example of identification of an alert and adaptation. The system may be configured to identify a variety of other patterns and apply one or more adaptations accordingly.

In some exemplary implementations, the system may provide a set of predetermined reporting profiles. A given user may be associated with one of the profiles based on the received context/behavior information (e.g., a user's preference on how the system should behave). For instance, an extra anxious user may like to alerts that are frequent, and sounds that are soothing because he wants to know where he is all the time, but at the same time does not want loud alerts. If the user is not responding the alerts or looking at the screen too often, the system may determine that behavior and change the alert settings accordingly (i.e., changing thresholds from 80 to 70 or vice versa). As another example, if the user is changing from normal to silent every morning at a specific time, the system can adapt to perform such adjustment automatically based on the historic information for the user.

In some exemplary implementations, the system may adapt based on a determination of how long it typically takes a particular patient to go from 100 mg/dL to 60 mg/dL or 200 mg/dL or 300 mg/dL based on time of day, day of week, or using other external sensor inputs. This prediction of risk estimation may be based on knowledge of insulin, exercise, and time of day/week. The goal of risk estimation is to determine if an individual is at risk (or has higher odds) of becoming hypoglycemic on a particular night. Whether one becomes hypoglycemia depends on a number of parameters such as, food, exercise in the past 24/48 hours, insulin on board, hormonal changes, and stress.

To perform the adaptation, a probability distribution of these parameters may be provided for an individual. For example, probability distributions for hypoglycemia based on information of one or more of the following: food, exercise, insulin on board, hormonal changes, and stress may be provided a priori and/or adapted for a particular patient based on patterns over time. Probability distributions may be provided for other parameters/information as well. A 'likelihood' estimate may then be generated by the system based on the probability distributions to determine if a person has less or more likelihood of becoming hypoglycemia. For example, if the person is normal and all his parameters/information described above are around their mean values (e.g., within the distribution), then the likelihood of being normal (which is a product of all probabilities) is high. If one or more parameters deviate from the mean, then the product deviates from the likelihood of being normal.

In one exemplary implementation, the parameters include:
1. Food consumed in the past 4 hours: N(mu1, sd1), with peak Probability of 0.1 at when food consumed is at mu1 (e.g., 100 g of carbs).
2. Insulin on board in past 8 hours: N(mu2, sd2), with peak Probability of 0.1 at when insulin at mu2 (e.g., 20 Units).
3. Exercise in the past 4 hours: N(mu3, sd3), with peak Probability of 0.1 at when the exercise is at mu3, (e.g., 2 hours intensive).

Assume for now these parameters are normally distributed with mean and standard deviation as noted. These values and probabilities are the normal levels for this person at which he is considered normal (i.e., his glucose is within the normal range, say 70-180 mg/dL). On a particular day, the likelihood of observing data when this person is normal is defined in Equation 1 and based on the example a parameters above.

$$L(\text{data/normal}) = \text{Prob(food)} * \text{Prob(Insulin)} * \text{Prob(exercise)} \tag{1}$$

If everything is at the mean (i.e., normal), the likelihood is highest, which in this example is 0.1*0.1*0.1=0.001. Suppose the system determines that the person ate a lot less food than normal on a particular day (e.g., 10 g of carbs). In this case, the probability value for 10g in his distribution is value much smaller than 0.1. For example, this can be 0.01. When this happens and if he did the same amount of exercise and took the same insulin, the likelihood of his being normal will now be 10 times lower or alternatively he is 10 times more likely to become hypoglycemia.

As described, the system adapts the model to a person's normal behavior. When inputs indicate a change, the system generates an estimate of how that change impacts the risk of becoming hypoglycemic. For the food for example, mu1 is the typical carbs one eats in a meal (e.g., 50 g) and sd1 would be the variation from meal to meal (i.e., sometimes one eats 45 g, sometimes 55 g, etc.).

Figure 3:
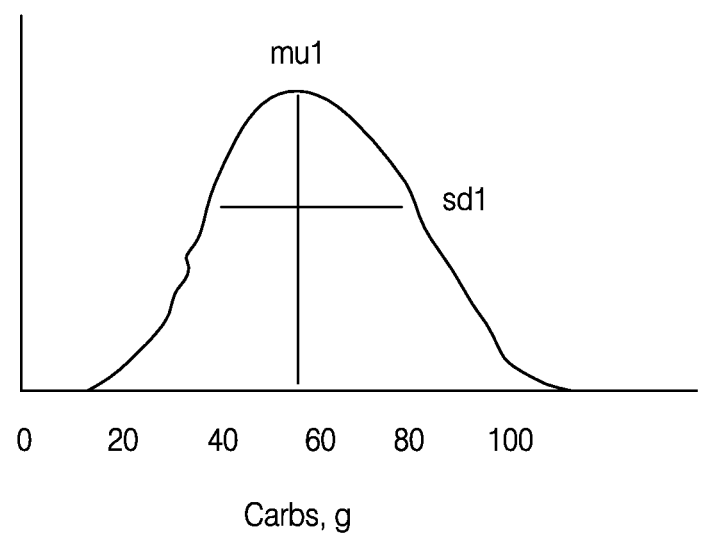
FIG. 3 shows a plot of the histogram (or distribution) of carbs in a meal for an individual over a period of 30 days.

FIG. 3 shows a plot of the histogram (or distribution) of carbs in a meal for an individual over a period of 30 days. The histogram shown includes a mean (mu1) and standard deviation of (sd1). The information for the graph may be used to adapt the reporting described above. For example, alert glucose threshold may be adjusted if it is determined the patient is located in an Italian restaurant.

Another example adaptation is to adjust the menu items based on their helpfulness to a patient in managing their disease. For example, the system detects how often a user accesses a particular menu item. As used herein, a menu item generally refers to a display selection or user interface control which provides information to a user of the device. Menu items may be fixed based on what the system developer believes is the frequency of access. However, as noted above, perception of useful items can vary from patient to patient and the determined format for the menus may not be useful for disease management of all people in the same way. Accordingly, the system can identify a frequency of access for each menu item. Based on the identified frequency, the presentation of the menu items may be adjusted. Adjustment may include re-ordering menu items, hiding menu items, increasing the presentation to be more or less prominent (e.g., font size), associating the menu item with a "hot-key" or the like. By the described features, the priority and presentation characteristics of menu items may be adapted.

As thus described, the system includes a set of reporting profiles that defines the behavior of alerts. These defined profiles are based on previously obtained information regarding different profiles that match peoples' preferences on average. Upon observing the actual behavior of a particular user when the user starts using the system, the system can adapt the profile to match the particulars of the user. The adaptation may include suggesting a new profile if the user specified a preference for a profile, but selected a profile which is not suited to the identified context/behavior detected by the system. The system can then apply the new, adapted profile that matches the user better.

FIG. 4 is a process flow diagram of a method of determining behavioral and/or contextual information for a patient. It may be desirable to capture inputs without the user having extra efforts/interactions. By configuring the system to capture behavior and/or contextual information from various inputs associated with user behavior and/or context surrounding use of the device, without burdening user to explicitly provide such information, the user will be more likely to use and benefit from the device. For example, a user can walk past a communication hub that has been installed in their house or car that will sync up the data inputs such as to the cloud/server. The system may be configured to organize the data and learn and organize the individual's behaviors. Goals or criteria may be identified based on the data. The information may be transmitted back to the device at user-specified intervals, daily, weekly, monthly, etc.

The process 400 shown in FIG. 4 may be implemented in whole or in part using a continuous monitoring system such as the devices shown and described in FIG. 1. The behavioral and/or contextual information determination process 400 may be implemented as a server process in data communication with a continuous monitoring device. The behavioral and/or contextual information determination process 400 may be implemented in hardware such as via a field programmable gate array or application specific integrated circuit or a microcontroller specifically configured to implement one or more aspect of the behavioral and/or contextual information determination process 400 described in FIG. 4.

The process of determining behavioral and/or contextual information uniquely identifies information useful for solving a long felt need of personalizing general purpose devices for healthcare use, or health care devices intended for use with a wide variety of user preferences, in a simple and intuitive manner. That is, not all users have the same preferences when it comes to personalization of a medical device, especially a consumer-driven medical device. Some users are tech savvy and enjoy reviewing large amounts of their health data; other users prefer a simpler interaction. Many fall in between and their preferences may be influenced by the context surrounding their interaction. Unfortunately, creating devices that are highly customizable also tend to be highly complex, and vice versa, therefore do not address the full spectrum of users. There remains a need for automatically and adaptively understanding the behavior and context of the user of a consumer-driven medical device that is highly intelligent and allows for simplicity of use. In one implementation, these needs are met by capturing contextual and/or behavioral inputs (402); tracking the behavior and/or contextual inputs over time to collect a database of information (404); processing the inputs to determine behavioral and/or contextual information about the patient (406); optionally providing an indication of the contextual and/or behavioral information (408) and/or optionally providing the behavioral and/or contextual information to any of the adaptive processes described herein (i.e., block 204 of process 200; block 504 of process 500 or block 602 or process 600), a device may be efficiently, intuitively and intelligently personalized for optimizing health care management and use, without requiring a complex or comprehensive understanding of technology, human behavior (or context) and health data that would otherwise extremely difficult, inefficient and likely impossible for a human to perform as is made possible by the systems and methods described herein.

At block 402, contextual and or behavioral inputs are captured. The inputs may be discovered or registered as described, for example above. Behavior input information may be obtained via the system. Behavior inputs can include an amount of interaction, glucose alert/alarm states, sensor data, number of screen hits, alarm analysis, events (e.g., characteristic associated with the user's response, time to response, glycemic control associated with the response, user feedback associated with the alarm, not acknowledging alerts/alarms within x minutes, time to acknowledgment of alarms/alerts, time of alert state), diabetes management data (e.g., CGM data, insulin pump data, insulin sensitivity, patterns, activity data, caloric data), free fatty acids, heart rate during exercise, IgG-anti gliadin, stress levels (sweat/ perspiration) from skin patch sensor, free amino acids, troponin, ketones, ketones, adipanectin, troponin, perspiration, body temperature, and the like. The inputs may be provided by a sensor in data communication with the monitoring device. In some implementations, the information may be obtained through an intermediary such as a remote data storage.

Contextual information which may be provided as an input to the system includes a person's biology, location, sensing surroundings (e.g., light, sound level), environmental data (e.g., weather, temperature, humidity, barometric pressure). The inputs may be received via peer-to-peer or mesh network via machine to machine communication as discussed above. Context information can include daily routine information (may change especially from weekdays to weekends) from calendaring application. Context information can include frequency of touching or grabbing the monitoring device, even if not interacted with, based on sensed motion of the device (e.g., accelerometer or camera sensor). Photos can provide contextual information. For example, photos of one or more of: a glucose meter reading, an insulin pen or pump JOB, a location (e.g., gym, park, house, Italian restaurant), or a meal may be used to provide context information. The photos may be processed to identify, for example, caloric intake for the meal shown in the photo. The type of insulin used may also be provided to the monitoring system as an input useful to adapt the system. Context may also be provided by basal or bolus settings provided to or determined by the monitoring device.

Other inputs to the adaptation process include exercise information from a fit bike or the like, glucose sensor information from a blood glucose (BG) meter or CGM, insulin delivery amounts from insulin delivery device, insulin on board calculation for the device, and other device provided or calculated information.

Hydration level, heart rate, target heart rate, internal temperature, outside temperature, outside humidity, analytes in the body, hydration inputs, power output (cycling), perspiration rate, cadence, adrenalin level, stress, sickness/illness, metabolic/caloric burn rate, fat breakdown rate, current weight, BMI, desired weight, target calories per day (consume), target calories per day (expend), location, favorite foods, level of exertion are additional examples of context/behavior inputs to the adaptive process.

For any of the above referenced behavior or contextual inputs, the system may be configured to receive and/or generate analytical metrics based on the inputs. For example, a composite value may be generated based on the glucose level, temperature, and time of day to generate an index value for the user.

As the system may provide goals, behavior information can include detected improvements or success rate of goals/criteria. It has been shown that people who look at historical glucose data have better diabetes management. The information can include time stamp to identify how often people look at their historical glucose data.

The initial inputs at block 402 may be internally (e.g., within the monitoring device) derived data such as sensor measurements, internal calculations and/or other information provided by the patient or known by the system at the initial query stage. For example, information about user interactions and outcomes (short term and/or long term) of that response may be identified.

The initial inputs may be used to generate a degree of confidence for adaptations/advice/guidance generated by the system for user. The degree of confidence can allow the user to specify a level of "fuzziness" in the adaptation, advice, guidance they are willing to accept. One way the initial input may be used by the system to generate a degree of confidence is to identify how confident a user is in the system being able to identify and adjust its operation based on the received behavioral, contextual, and physiological information. For example, a person may completely trust the system to automatically adapt over time without any user intervention while another person may trust the system to adapt certain aspects of the system (e.g., menu items), but not have confidence for adjusting analyte thresholds without approval.

In some implementations, each adaptation identified may be associated with a confidence score. The confidence score may be based on one or more of: the amount of data received from the user that was included in the determination of the adaptation, the amount of data received from the device that was included in the determination of the adaptation, the amount of data received from the community of users or users with similar health concerns as the user of the device that was included in the determination of the adaptation, or a characteristic indicating the level of sophistication of usage for the user, for example. These amounts may be compared to respective threshold values to determine a relative confidence score for the proposed adaptation. As such, the more data that is available, the more reliable the adaptation is likely to be.

Based on the confidence score, and, in some implementations, the user confidence level (e.g., trust level in the system), the system may be configured to automatically apply (within adaptive reporting process 200, adaptive goal setting process 500 or adaptive guidance process 600) the adaptation, apply the adaptation after confirmation, or not apply the adaptation at all.

At block 404, the behavior and/or contextual inputs are tracked over time to collect a database of information (builds record of input). The system may periodically store pre-identified inputs, wherein a record of user-specific pre-identified inputs is created. By tracking over time, patterns can be extrapolated. For instance, behavioral information acquires meaning when a track record of certain use patterns over time is provided. Similarly, contextual information is traceable and associated with time (e.g., user typically at school from 9 AM-3 PM).

In some implementations, the tracked data may be collected in a specially adapted database on the device. In some implementation the storage may be in data communication with the device (e.g., in the cloud or other devices (e.g., accelerometer, sleep tracker)). The collection may be directly from the sensor or via an intermediate module such as a calendar.

The collected information may include information collected by users with the same condition as the user of the device. For example, for a patient query, the system is configured to respond with a weighted response where x % weight is given to the user's past data and y % weight is given to data of other users under the same condition such that the sum of x and y is 100%. Historical referencing and learning based on the user themselves, and how they compare to a broader population, provides inputs that may be useful to the adaptation process (within adaptive reporting process 200, adaptive goal setting process 500 or adaptive guidance process 600) to better identify how trend or health projects forward and what interventions/actions/steps are possible and most successful at resolving situation or maintaining a desired state.

At block 406, the inputs are processed to determine behavioral and/or contextual information about the patient.

The information may be collected into a record for the patient. The processing may be periodic such as according to a schedule, or event driven (e.g., upon receipt of new input data, during idle system times). The system is configured to identify patterns of behavioral or contextual information (e.g., user interaction with the physiological information display). The identification may be based on recognition of predetermined patterns of input data (e.g., one or more values or ranges of values associated with a behavior or condition). For example, if the input is an accelerometer, and the detected speed is 70 miles per hour, the speed input information may be associated with the behavior of driving. In some implementations, the system may include or communicate with an artificial intelligence module adapted to extrapolate contextual and/or behavioral information associated with patient. The generated patient information may be used as contextual and/or behavioral information for further adapting the device, such as described above in reference to: block 204 of the adaptive reporting process 200; block 504 of the adaptive goal setting process 500; and/or block 602 of the adaptive guidance process 600.

The example method shown in FIG. 4 includes block 408 which provides an indication of the contextual and/or behavioral information identified. Block 408 may be omitted in some implementations. As some information may be collected automatically, estimated, or inferred, block 408 serves, in part, as a "sanity check" on the information and adaptations based thereon. By providing an indication of the identified information, users (e.g., the patient, doctor, caregiver, etc.) can provide some feedback regarding the identified information. For example, the indication may be provided in the form of a question on a user interface or report with a selection of responses or open ended response. Example questions include "Were we right?" "Should we act on this information?" or the like.

In some implementations, the indication may be transmitted to another device, such as an insulin pump, medical record, or other system included in the care plan for the patient. Transmitting the indication can help these systems (or the monitoring system) better estimate and understand their capabilities, adapting operational characteristics based on good estimates/decisions/intuition, inconsistent estimates/decisions/intuition or bad estimates/decisions/intuition. The monitoring device may be configured to even respond with teachings/learnings to help the other devices improve their estimates/decisions/intuition.

As one example, an interactive avatar displayed on the device could display a prompt to the user inquiring, "Are you at home?" or "Would you like to change your alarm settings when you are at home?" Based on the response, the device could inform insulin pump about context or behavior that might influence which control algorithm runs, which basal profile to start with, where to send alerts, when to open the loop of a closed loop control system (e.g., adjusting to include validation or transition to semi- or non-closed state), etc. The device may be configured to transmit this information to the cloud for collection in a database (preferably in de-identified format), or to an electronic medical record Providing the indication may include speech recognition, taking verbal queues, and/or use natural language processing. For example, the response to the indication may be a delayed "I think so." Such indecision may be identified based on the received audio waveform. This indecision may be used to discount the indicated information. For example, if the behavior identified was "ice fishing" and the received response was a slow "I think so", the system may be configured to consider this behavior, but for limited purposes.

As described, in providing the information, further requests and/or processing of additional information/inputs from the user may be performed based on data processing/feedback loop. This allows the adaptation process to work with the information provided and obtain the inputs most likely to yield meaningful adaptations for the user.

The system can be configured to remind the user that looking at historical data is an important part of their diabetes management. The reminder may be included as a message for periodic display via the device. In some implementations, the reminder is combined with other behavior/context pattern recognition to generate a message for display to the user about their historical data.

Consider the following example including aspects of FIG. 4. A user inputs data into their personal calendar which is registered to communicate the calendar data to the monitoring device. Upon analyzing the calendar data via, for example, key word searching, the system identifies that the user's upcoming events includes exercise, such as a planned yoga class. The monitoring system may see this class recurring weekly. Accordingly, the monitoring system may adapt to the exercise patterns and make recommendations such as, "Would you like to start your temp basal rate now if you plan on exercising in 1 hour?" one hour prior to the scheduled class. As another recommendation, the system may present the user a message such as, "Consider eating a snack now if you are going to exercise in 1 hour." The message may be selected based on previous exercise patterns from similar activities. In some implementations, the input information may be obtained from social media calendars or events planning systems, such as Facebook™ events or Evite™ invitations.

By determining an upcoming event/behavior/context (within process 400), a corresponding adaptation may be provided. For example, if an activity such as sustained exercise, long bike rides, hiking, etc. is identified, a database of recommendations may be queried based on the anticipated event as well as other patient specification information to identify an appropriate suggestion and time to provide the suggestion. For example, the system may identify a reminder for the patient to eat a small snack half-way through to prevent hypoglycemia and/or refuel. The suggestion may also include possible snacks based on information from a smart refrigerator regarding the available food items in the refrigerator.

The monitoring device may be configured to identify location information. The location information may be obtained directly from a positioning device included in or in data communication with the monitoring device. Over time, the location information for a patient may be used to help understand life patterns and potentially even activity. For example, the locations may be geocoded to identify a business that takes place at a given location (e.g., gym, Italian restaurant, grocery store, movie theater, etc.). Location information may be utilized by the adaptive reporting process (200), the adaptive goal setting process (500) and/or the adaptive guidance process (600) to determine location-based adaptations and/or goals.

Additional inputs may include audio inputs such as recordings of the user. The monitoring system may be configured to identify stress, panic, or anger by analyzing the recordings (e.g., wavelength, tempo, pitch, volume, length of conversations). Stress, panic, or anger may also be identified based on physical behavior. In general, the more animated a person is, the higher the degree of excitement. Accordingly, motion information may be captured by the device (e.g., from an accelerometer) and compared to an activity threshold. The activity threshold may be a standard threshold or adapted to the patient. If the activity level detected exceeds the threshold, then the patient may be identified as high excitement and thus stressed, panicked, or angry. The thresholds may be calibrated for each of these three emotions (or other emotions).

Figure 5:
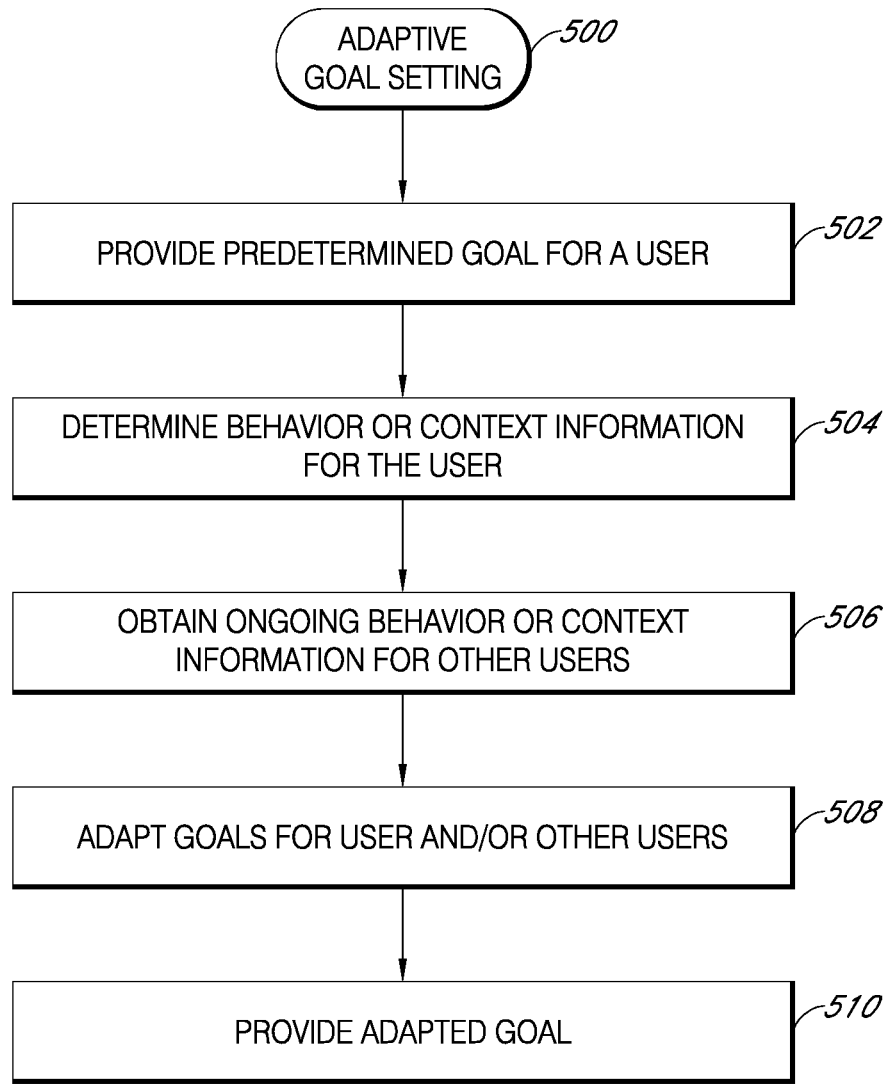
FIG. 5 is a process flow diagram of a method of determining goals or criteria for use in one or more aspects described.

FIG. 5 is a process flow diagram of a method of determining goals or criteria for use in one or more aspects described. The process adaptive goal setting process 500 shown in FIG. 5 may be implemented in whole or in part using a continuous monitoring system such as the devices shown and described in FIG. 1. The adaptive goal setting process 500 may be implemented as a server process in data communication with a continuous monitoring device. The adaptive goal setting process 500 may be implemented in hardware such as via a field programmable gate array or application specific integrated circuit or a microcontroller specifically configured to implement one or more aspect of the adaptive goal setting process 500 described. The goals or criteria determined by the adaptive goal setting process 500 can be provided for use in one or more of the processes described such as block 206 of the adaptive reporting process 200 and/or block 602 of the adaptive guidance process 600.

The process of providing automatic adaptation of goals or criteria based on behavioral and/or contextual information can solve a long felt need of personalizing general purpose devices for healthcare use, or health care devices intended for use with a wide variety of user preferences, in a simple and intuitive manner. That is, not all users have the same preferences when it comes to personalization of goals or criteria of physiological information of a medical device, especially a consumer-driven medical device. Some users may be particularly motivated and quickly achieve certain goals; while other users may take more time. Many users fall in between and their preferences may be influenced by the context surrounding their interaction. Unfortunately, creating devices that are highly customizable also tend to be highly complex, and vice versa, therefore do not address the full spectrum of users. There remains a need for automatically and adaptively understanding the behavior and context of the user of a consumer-driven medical device that is highly intelligent and allows for adaptation of the goals and criteria. In one implementation, these needs are met by providing a predetermined goal for a user (502); determining behavior or contextual information for the user (504); optionally obtaining ongoing behavior or contextual information for other users (506); adapting goals for the user and/or optionally for other users (508) and providing an adapted goal or criterion (510), a device may be efficiently, intuitively and intelligently personalized for optimizing health care management and use, without requiring a complex or comprehensive understanding of technology, human behavior (or context) and health data that would otherwise extremely difficult, inefficient and likely impossible for a human to perform as is made possible by the systems and methods described herein.

"Adaptive goal setting" generally refers to the process, quality, or act of updating or changing the goals or criteria based on received information such that a goal or criterion is adjusted. In some implementations, the adaptation is based on predictive inferences drawn from the information collected for the associated user. An adaptive goal setting system or method may be contrasted with a reactive goal setting system or method. Whereas a reactive goal setting system or method may provide a single reactive adjustment in real time based on a single event or selection (e.g., in reaction to a stimulus), an adaptive goal setting system or method anticipates the event based on the previous behavioral or contextual patterns identified for the user over time and makes an ongoing adjustment to a goal or criterion based thereon.

A goal may generally refer to a desired outcome such as more frequent checks of historical data. For each goal, there may be one or more criteria indicating whether the goal has been achieved. For example, if the goal is increased frequency of historical data checks, the criteria may include: desired number of checks per unit of time and number of checks for previous unit of time. The goal may identify a relationship between the criteria. For example, the goal may include an indication that the number of checks for a previous unit of time must be greater than or equal to the desired number of checks per unit of time. More complex relationships may be defined for a goal. Goals may be organized hierarchically such that a higher level goal cannot be achieved without first satisfying a lower level goal.

Examples of goals include goals focused around setting up the system, goals for setting up thresholds, sensor wear time goals, sensor session goals (e.g., first sensor session completed, first 3 days on sensor), device calibration goals, alarm acknowledgement goals. Some goals may be selectable goals that correlate to other contextual inputs. e.g. don't go low when exercising. Goals may be context sensitive. For example, a goal may be based on detected location. For example, don't go low when at the gym. Further examples of goals include insertion goals such as learn how to use applicator, how to wash hands, place sensor, start sensor session. Removal/disposal goals such as how to get the most out of the session's data, how to dispose of sensor, may be established and monitored by the system. Still further examples of goals include data goals (e.g., how to read data, how to set up alarms), community goals (e.g., how to provide/give support to others), daily goals (e.g., how to address eating behaviors, how to address exercise behaviors, sleep behaviors), device maintenance goals—how to clean transmitter, how to charge receiver, how to customize transmitter, how to change alarms, how to calibrate), treatment goals (e.g., how to count carbs, identify target range, calculate insulin on board).

Another example of a goal includes input specific goals such as for pediatric patients who are moving from having their diabetes managed by their parents to achieving greater levels of self-management to prepare them for life on their own. Carb counting goals or use of photo software for counting carbs can be identified for these patients to help patients actually use the system and take ownership of their diabetes management. As younger users may respond more positively to rewards, the adaptation process may also include offering rewards for positive behaviors. Furthermore, the system may be configured to show younger patients how various activities affect their BG levels so they can understand the patterns themselves. For example, a time-lapsed animation may be generated by the system based on the obtained inputs (e.g., behavior, sensor, and context). To provide peace of mind to the parent, the system may include further configuration to transmit the information via progress reports for the child. Accordingly, parents can feel more comfortable with giving their child more autonomy. Autonomy can be a two-way street because a child patient cannot achieve total self-management if the parent is consistently managing the child's care. In some circles, such overbearing parents may be referred to as a "hover parent."

Similar goals may be established for older patients who are also being cared for by a family member or care provider. Using the training example, the goals may provide a way for a heath care team to monitor their patient's progress and provide feedback to other loved ones/family members caring for an older adult.

The list that follows identifies further goals which may be provided:

1. How long maintain no hitter?
2. How many consecutive nights without hypo?
3. How many post-meal sessions without breaking a threshold mg/dL?
4. How long keeping rate of change under a threshold mg/dL/min?
5. Less than a threshold number of severe hypoglycemic event during a time period (e.g., in the last month)?
6. Less than a threshold number of hypoglycemic events in a time period (e.g., week)?
7. Less than a threshold number of hyperglycemic events in a time period (e.g., week)?
8. Glucose standard deviation less than a threshold value in a time period (e.g., the last week).
9. Time in target increased by a threshold amount (e.g., percent).
10. Time hypoglycemic event decreased by a threshold amount (e.g., percent).
11. Time hyperglycemic event decreased by a threshold amount (e.g., percent).

At block 502, a pre-determined goal is provided. The pre-determined goal may be installed at the time of manufacture. The pre-determined goal may be based on the intended use for the device, such as glucose monitoring. The pre-determined goal may be installed when the device is initialized the patient based on some basic input information received (e.g., age, condition, language). The initial goals may be established based on received responses selecting goals from a list of predetermined goals.

In some implementations, a care provider may transmit information via an interface identifying goals for the patient. For example, a goal may be to work on food behaviors and nothing else, for the next 3 months. Goals may be provided via the interface by a member of the patient customer support (PCS) team working with the patient. For example, the goal may originate from a patient request such as "I can't seem to get the sensor insertion location to be comfortable." As one way to assist the patient, the PCS member may transmit a goal to work with how and where the sensor is inserted (e.g., sensor should be moved to right side.).

As described thus far, the goals are associated with a single user/patient. In some implementations, patients may be logically grouped into communities such as online communities, communities of users, social media networks, patient care communities, or the like. By associating a goal with the community, users can compete within the community and with other communities to achieve goals. Such social interaction can increase usage of the device and enhance overall health outcomes.

To identify goals, the device may be configured to operate in a training mode. The training mode may be identified as a period of time (e.g., two weeks from the first power on). During the training mode, the device may be configured to collect inputs to identify and select a goal from a list of programmed goals. In some implementations, the device may not collect inputs but utilize a batch record import including behavior and context information for the patient. The imported information may be then used to identify one or more predetermined goals.

In some implementations, the system may include default goals. For example, a default goal could be defined which is applicable to a wide variety of potential outcomes, such as glucose variability, time a patient takes to transition from a first glucose level to a second glucose level ("turn around time"), "no hitter" days, A1c reduction, interaction with the data, consistency of sensor wear, calibrating on time, insulin delivery requirements, and the like.

As described, information for the device may be received via an interface. An interface may include, but is not limited to, a visual interface such as a graphical user interface including one or more fields configured to obtain inputs to the system. In some implementations, the interface may be a voice interactive interface.

The device may provide a search capability. The device may receive query parameters for searching the device or other entities in data communication with the device (e.g., content library, map server, internet search engine, etc.). As the activity of searching may be included as a behavioral input, an adaptation may be based on the queries submitted. For instance, a new goal may be identified based on a natural language query provided to the system. For example, if a search is detected including the query "How do I avoid afternoon lows?" a corresponding goal may be set to help the user achieve the goal of avoiding afternoon lows. The goal may be identified as discussed above, by comparing the received input information to one or more keywords associated with the goal.

At block 506, ongoing behavioral and/or contextual information from other patients/metadata is obtained. As previously discussed, information for the patient and other patients with similar conditions to the patient may be stored remotely (e.g., in the cloud). Users identified as facing an issue may provide suggestions of solutions that have worked for them. When the system receives a query, (e.g., how do I prevent a rebound hypo), the system takes their prior cases of rebound along with all inputs available (e.g., what did the user eat, what was the level of different hormones, etc.) and compares it to big data in the cloud of other users who avoided the same condition and present actionable recommendations. The comparison may obtain the aggregated data and perform the matching on the device. In some implementations, the comparison may be performed in a server-client mode. In this mode of operation, the query may be augmented with some additional, patient specific information and transmitted to an analytics engine in data communication with the device. Once processed, the response may be received by the device. By querying past user and broad population data, a more robust response may be provided.

At block 504, contextual and/or behavioral information for the user is collected from the user. FIG. 4 provides more detail on how behavior and/or contextual inputs may be captured, tracked, determined and indicated, any of which may be applied as a subroutine at block 504 of the adaptive goal setting process 500. Namely, contextual and or behavioral inputs may be captured as described at block 402; the behavior and/or contextual inputs may be tracked over time to collect a database of information as described at block 404; and the inputs may be processed to determine behavioral and/or contextual information about the patient as described at block 406; based on which an indication of the contextual and/or behavioral information may be optionally provide as described at optional block 408; and/or the contextual and/or behavioral information directly inputted to block 504 described herein. The collection of information may include doctor prescription, PCS team goal generated based on a phone call with patients, or a goal the user assesses the need to perfect. Such information may be collected actively (e.g., through responses received through an interface of the device from a user) or passively (e.g., via sensors).

At block 508, based on the information obtained about the patient (block 504) and others similarly situated (block 506), one or more goals may be adapted. The adaptation may include altering criteria for a goal. The adaptation may include identifying additional goals to include for the patient. The adaptation may include removing a goal for the patient. The adaptation may include a consideration of who initially defined the goal (e.g., default, doctor, PCS team member, self, or team). For example, if the goal was a doctor identified goal, the goal may not be automatically adaptable. For such goals, a suggestion of an adaptation may be provided to the doctor and, upon confirmation, applied. Generally speaking, the patient should select goals and the system should suggest goals. In some implementations, the system may be configured to receive a patient confirmation for adding suggested goals and/or adaptations to existing goals.

The system, in some implementations, may be configured to adapt a predetermined goal based on criteria. For example, if user has achieved a first goal, the goal may be adapted to make the goal a bit tougher. Or if the user does not achieve a goal, the system may adapt the goal to reduce the stringency of a criterion for the goal so that success can be achieved and/or perceived. Rewards for achieving a goal may include badges. Badges may represent virtual identifiers associated with the user/patient. Badges may be appointed or a person's profile can be elevated to show new status based on achieving goals.

The system may be configured to automatically identify new predetermined goals based on inputs and criteria from other factors, such as food, exercise, insulin intake, etc. as the information becomes available to the system.

In some implementations, the system may include pattern recognition module. The pattern recognition module may be configured to look for differences between the received input for a user and patterns associated with typical users. For example, the system may consider a previous data set from a patient (e.g., several weeks of data) and establish a pattern of glucose behavior as a basis or goal against which to compare future data. When the glucose reading is identified outside the basis or goal determined from the pattern of glucose behavior, an alert could be sent to indicate something abnormal was occurring. This may be relevant, for example, for type 2 diabetics who have no medication or are taking an oral medication. The behavior modification and identification of patterns are substantially different than normal patients. This pattern deviation may be desirable feature for patients who have difficulty complying with their care plan.

As an example, consider a person who wears a CGM. A care giver looked at CGM graph on the 4th morning. The glucose reading was higher than normal and more variable. After some discussion, the person realized he had forgotten his medication that morning. The patient may not consider the missed dose until the care giver asked him about it, even though he had seen the data. The CGM may be adapted via pattern recognition to identify the change in pattern and alert the patient.

The adaptive approach techniques described could also be used to set adaptive target glucose levels for patients (e.g., for non-insulin using diabetics). The target levels that would display and potentially alert may be based on the previous history and the goals the patient was trying to achieve. Rather than setting a static level for an alert, it could be dynamically changing to reflect improvements and changes to a target healthy level.

The system may be configured to identify trouble-spots or knowledge gaps based on the received behavior or context information vis-à-vis goals. Based on the track record, the system may be configured to adapt by creating goals to help users improve/learn in these areas. The created goals could be prioritized (e.g., more important goals to the patient's health condition) or random.

At block 510, in some implementations, the adapted goal may be presented. For example, the adapted goal may be used in the context of the adaptive reporting process 200 shown in FIG. 2 such block 206 whereby the adapted goal is compared to the behavioral and/or contextual information. Presentation of the adapted goal may include a side-by-side comparison of the existing goal and the proposed adaptation. A message may be received by the system, acknowledging or declining the adaptation. In this way, a user may exercise control over the changes identified by the system. The acknowledgment may be received via a visual interface such as a web-form or social media network. The presentation and/or acknowledgment may occur out of band. For example, an email or text message may be generated including the goals and proposed adaptations. The email may include a unique identifier which can be included in a response email message from the user to accept the changes. In such an implementation, an email server is configured to receive the message and automatically transmit a message to the monitoring device acknowledging or rejecting the adaptation.

The monitoring device may include a health optimization configuration which adjusts the operation of the monitoring device. This configuration value may be provided to the adaptation process as an indicator of how much the user wants the system to adapt (e.g., optimize) their goals and/or how much the user wants to interact with the device regarding setting or confirming their goals.

The presentation of goals at block 510 may, in some implementations, include suggestions by an avatar, selections from a menu. The presentation at block 510 may be triggered by an adaptation. For example, when an adaptation is identified and/or applied, the presentation at block 510 may occur. In some implementations the presentation at block 510 may be based on time of day (e.g., when, based on received inputs, most issues seen), location (e.g., where, based on received inputs, the most issues are seen), weather (e.g., temperature that causes the most issues), and the like.

While goals may be presented to the user of the monitoring device, goals may additionally or alternatively be presented to an electronic medical record (EMR), to a parent/caretaker, or to a closed loop control system (e.g., for adjusting settings, variables, inputs, alarms, interaction with patient, etc.). In some implementations, the presentation may also include providing the goal to members of a group the user is a member of. In this way, new goals useful to one user may be contributed to the community for use by other users.

Figure 6:
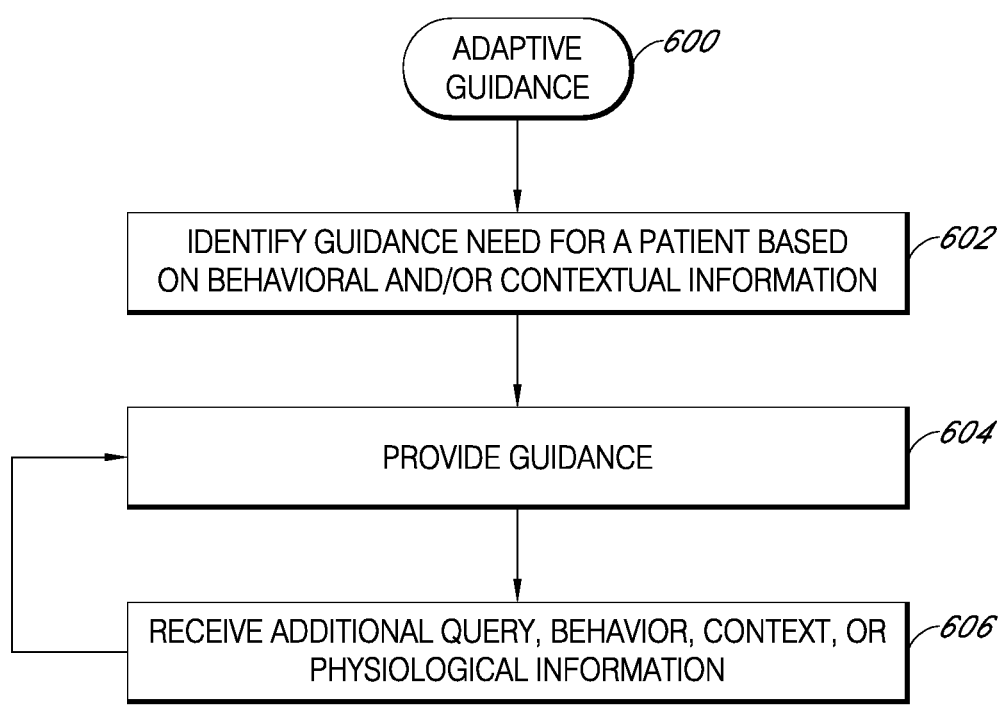
FIG. 6 is a process flow diagram of a method of providing patient training, improvement in diabetes management, and/or short term recommendation.

FIG. 6 is a process flow diagram of a method of providing patient training, improvement in diabetes management, and/or short term recommendations. Collectively the provided content may be referred to as patient training. The patient training may be selected based on the goals/criteria associated with the patient.

The adaptive guidance process 600 shown in FIG. 6 may be implemented in whole or in part using a continuous monitoring system such as the devices shown and described in FIG. 1. The adaptive guidance process 600 may be implemented as a server process in data communication with a continuous monitoring device. The adaptive guidance process 600 may be implemented in hardware such as via a field programmable gate array or application specific integrated circuit or a microcontroller specifically configured to implement one or more aspect of the adaptive guidance process 600 described.

The process of providing adaptive guidance based on behavioral and/or contextual information solves a long felt need of personalizing general purpose devices for healthcare use, or health care devices intended for use with a wide variety of user preferences, in a simple and intuitive manner. That is, not all users have the same preferences when it comes to personalization of guidance or training of physiological information of a medical device, especially a consumer-driven medical device. Some users may be particularly motivated and quickly understand many basic concepts associated with use of the medical device; while other users may require more guidance or training. Many users fall in between and their preferences may be influenced by the context surrounding their interaction. Unfortunately, creating devices that are highly customizable also tend to be highly complex, and vice versa, therefore do not address the full spectrum of users. There remains a need for automatically and adaptively understanding the behavior and context of the user of a consumer-driven medical device that is highly intelligent and allows for adaptation of the guidance or training. In one implementation, these needs are met by identifying a guidance need for a patient based on behavioral and/or contextual information (602); providing guidance to the user (604); and receiving additional queries, behavior, context or physiological information (606), a device may be efficiently, intuitively and intelligently personalized for optimizing health care management and use, without requiring a complex or comprehensive understanding of technology, human behavior (or context) and health data that would otherwise extremely difficult, inefficient and likely impossible for a human to perform as is made possible by the systems and methods described herein.

"Adaptive guidance" or "adaptive training" generally refers to the process, quality, or act of providing guidance based on received information associated with behavior or context of the user. In some implementations, the adaptive guidance is based on predictive inferences drawn from the information collected for the associated user. An adaptive guidance system or method may be contrasted with a reactive guidance system or method. Whereas a reactive guidance system or method may provide a single reactive guidance in real time based on a single event or selection (e.g., in reaction to a stimulus), an adaptive guidance system or method anticipates the event based on the previous behavioral or contextual patterns identified for the user over time and makes an ongoing adjustment to the guidance or training based thereon.

The adaptive guidance process 600 identifies and provides adaptive guidance for the patient related to use of the continuous monitoring system and/or management of the disease state associated with the monitoring. The guidance may be based on an identified training need based on received inputs for the patient (behavior and/or context information). The adaptive guidance need may be identified based on a query submitted by the patient via a search function included in the monitoring device. For example, a natural language query may be received by the monitoring device. Textual processing of the query may identify keywords. The keywords for the query (and, in some implementations, historical keywords) may be used to identify concepts which the patient asks a lot of questions about. The volume of questions may indicate more training is needed on the topic. In some implementations, the natural language queries may be received via a provided preselected query format such as "Predict overnight glucose levels and insulin requirements," "How do I adjust basal insulin settings?", "How much/type/timing insulin to bolus?", "How much/type/timing of exercise?", "How much/when/where/what to eat?

At block 602, a need for guidance is identified based on behavioral and/or contextual information obtained for the user. The obtaining may be performed as described with reference to FIG. 4 may be provided as a subroutine herein. Namely, contextual and or behavioral inputs may be captured as described at block 402; the behavior and/or contextual inputs may be tracked over time to collect a database of information as described at block 404; and the inputs may be processed to determine behavioral and/or contextual information about the patient as described at block 406; based on which an indication of the contextual and/or behavioral information may be optionally provide as described at optional block 408; and/or the contextual and/or behavioral information directly inputted to block 602 described herein. As discussed above, the behavior and/or contextual information may be received from an external device, collected by a sensor, or determined based on input information. The information may include a query received via the monitoring device. As discussed, in some implementations, weighting associated with each information element may be obtained. For example, contextual information may be weighted by a patient's personal preferences such as "I prefer organic foods instead of processed," "I'm a vegetarian," or "I like running instead of biking." Based on these preferences, whether expressed directly or identified based on behavior and/or context, weights may be adapted and assigned for contextual inputs and how much influence a particular input will have the criteria evaluation process during the search. Criteria for initiating the training process may be predefined in the system, wherein certain behavior and/or context information define criteria for identifying a training need of the patient.

Other questions which may identify the opportunity for additional training include:
1. When/what should I eat or drink to [exercise description here]?
2. What should I do today to meet my goal of losing weight?
3. Recommended restaurants or foods, servings and exercise
4. Can I substitute insulin with exercise? How much?
5. What would be my glucose in [number] minutes?
6. Based on input information received from a navigation system, can I complete the route without food?
7. If not, when should I eat? How much?
8. Suggest a restaurant on the route.
9. What is my estimated morning glucose?
10. What do I need to do to make that estimate x?
11. How do I treat this hypo/hyper?
12. What should I buy (or stop buying) at the grocery store?
13. Automatic grocery store list Additionally or alternatively, a training/guidance need may be identified at 602 based on the comparison of behavior or context information with a goal or criteria at block 206. For example, if the goal for a patient is to increase interaction with the device (and optionally adaptations to the reporting style do not result in progress toward achieving that goal), the training process may be initiated, whereby a training need (increased interaction with the device) is identified, and training (adaptive guidance) regarding how to best interact with the device is provided (604).

Additionally or alternatively, a training/guidance need may be identified at 602 based on the adaptive goal setting process 500, which is based on the determination of behavior or context information (within behavioral and/or contextual information determination process 400). For example, adaptation of goals (at 508) based on behavior/context may identify a training/guidance need (602) and adaptively provide guidance (604) toward the adapted goal. In some cases, wherein the adapted goal is more stringent than the previous goal, a training/guidance need may be identified (602) that adaptively provides guidance (604) on how to achieve the adapted goal. In some cases, wherein the adapted goal is less stringent than the previous goal (e.g., resulting from continual failure to meet the previous goal), a training/guidance need may be identified (602) to provide adaptive guidance (604) to the user in improving their performance towards achieving the goal. In some cases, wherein the adapted goal is a new type of goal for the patient, the training/guidance need maybe identified (602) to provide adaptive guidance for the patient (604) towards achieving the goal.

As a part of the behavior and/or contextual information gathering, a natural language query may be processed, along with physiological information and/or behavioral/contextual information. By combining the processing of physiological information and behavioral/contextual information, processing of queries (e.g., natural language queries or structured language queries) may be more personally and contextually answered.

Natural language query may take the form of a question received from the user by the system. For example, "I am hungry, what should I eat?" A natural language query, however, need not be in the form of a question. Providing a statement may trigger a query based on natural language processing of the received statement. For example, the statement "I am going to exercise now" may cause the system to determine that the user tends to hit a glucose low thirty minutes after beginning exercise. For such a user, the system may provide a message suggesting, "You may want to eat x carbs and I'll set an alert reminder in 3 hours to check your glucose levels" to help the user avoid the low.

In some implementations, processing the query may include artificial intelligence processing. One artificial intelligence technique which may be applied is "back propagation." In back propagation processing, criteria and input for affecting change on the system are weighted. The system dynamically adjusts the weights based on such things as how often an input is encountered, inversely decreased if a different weighted input is increasing, increase/decrease based on the passage of time, proportioned by one or more factors (e.g., user preferences, time of day, weather).

In the context of natural language queries, the system is configured, in some implementations, to adapt the weighted criteria. The weighting may be based on the number of time a question was repeated, the number of times a food was purchased based on system's recommendations, and/or turn off a recommendation for meats after some number of requests for vegetarian diet/restaurants.

At block 604, an adaptive guidance (and/or adaptive training) is provided for the identified need based on the behavior and/or context information for the patient. In some implementations, e.g., based on the identified need, physiological information of the patient in conjunction with the behavioral and/or contextual information is considered in processing the adaptive guidance. By considering both physiological information as well as behavioral/contextual information from the continuous monitoring system, training and/or guidance can be more personalized without bothering the user with a plurality of questions to be answered. In implementations featuring a structured language query, only the initial question is structured and the remaining information may be provided as part of the query is determined or collected as described above.

The adaptive guidance generated at block 604 may include answers to natural language query, e.g., recommend a salad from one of the following local restaurants: x, y or z; drink X ounces of Y in 1 hour; etc. The recommendation may be based on a query of a database of information coupled with the monitoring device. In some implementations, the query may be transmitted to a server for processing and the response received by the monitoring device.

The guidance may be provided not only to the user initiating the query but also to a parent, a child (for older adults), a loved one, a doctor, a certified diabetes education (CDE), a health insurance company, support group in social media, etc. For any age user (adult or pediatric) providing family members, loved ones, or heath care team this information may help provide those uses with a greater peace of mind, lessen the "diabetes police," and help a child obtain more autonomy from their parents, if the parent is comfortable with the child's training/diabetes knowledge progression.

The guidance may include activating features of the monitoring device such as placing a call to a doctor or a spouse/parent/friend. A feature of the system may be activated in response to a prompt. The system may select the prompt based on the behavioral and/or contextual information for the user. Example prompts include:

"Are you going to exercise now? You may want to eat x carbs and I'll set an alert reminder in 3 hours to check your glucose levels"

"Did you just eat?" About how many carbs were in the meal? Was it a simple carb meal or a complex meal with fat/protein? Consider taking insulin or x units of insulin."

"Are you driving? We suggest taking a brief break to have a snack."

In some implementations the training guidance and/or response may be provided through an avatar, which guides the user through training, tips, assistance and/or otherwise provides information useful to help answer the patients' question and/or provide training to address the identified training need.

At block 606, additional natural language, behavioral and/or contextual feedback may optionally be received. The feedback may include comments on the response. The comments may be transmitted via the monitoring device. The system may prompt the user for comments to get as much personalized information as possible from the user without requiring explicit user interaction (i.e., without necessarily asking direct questions). As shown in FIG. 6, the adaptive guidance process 600 may return to block 604 for further processing.

The feedback information may help refine a query. For example, expected duration of exercise, level of exertion, what did you have for breakfast, carbohydrate in-take, or a relative state (e.g., sick, stressed, excited on a scale from 1-10) may be obtained. The system may be configured to obtain the additional information and re-process the search with the additional information. In some implementations, the prompt for additional information may be based on the number of results for the initial query. For example, if too many hits are found for the query "how do I reduce my weight" for the patient, feedback on preferred exercises or foods may be obtained to help narrow the results.

The described methods and systems may be applicable for diabetes management. In the context of diabetes management, personalized assistance in maintaining analyte levels within a target range or getting to a desired target range is provided by the described features. Pre-specified queries related to: how to adjust basal insulin settings, how much/type/timing insulin to bolus, how much/type/timing of exercise, and/or how much/when/where/what to eat may be included in the system. The system may process input information from a variety of sources such as caloric intake derived from photo analysis software, a body metric that can be measured or unique shapes to glucose trend graphs, exercise information from a fit bit or the like, glucose sensor information from BG meter or CGM, insulin delivery amounts from insulin delivery device, insulin on board calculation and/or other device provided or calculated information. The systems and methods may also obtain information from personal calendar or social media sites the person is associated with. The adaptations are based on machine learning of patterns such as weights. The system and methods further include feedback which allows requests for additional information (e.g., Where are you located?). Aspects described further provide outputs including answers to question (e.g., recommend a salad from one of the following local restaurants: x, y or z.).

It has been shown that people who look at historical glucose data have better diabetes management. One non-limiting advantage of the described system and methods includes capturing a time stamp of how often people look at their historical glucose data. If a user has not looked at their historical data in a given period of time, the system can adapt the type, frequency, and format of reminders for the user. The reminder can include information that looking at historical data is an important part of their diabetes management. This could be combined with other pattern recognition to generate information about the user's historical data.

Diabetes management may be performed by a person through their behavior and actions. The adaptations and feedback may be used to help people manage their condition. Diabetes management may also be implemented using control systems such as closed loop control systems. By providing behavioral and contextual information for one or more users of the system, the system can adapt overtime to provide more effective, accurate, and tailored management of an individual's condition.

The described features may be applied in the context of non-diabetics and type 2 weight loss. A simple target calorie intake may be determined based on your calorie expenditure. Goals may include losing a certain number of pounds over a period of time. If your goal is to lose 10 pounds in 3 weeks, you would need to eat 500 calories less than you burn per day. Each day, the calorie expenditure is recorded and the next day's calorie intake is adaptively generated.

This can be extrapolated to glucose targets for type 2 non-insulin using diabetics. The system or method may be configured to analyze the glucose, calorie, and exercise behavior and/or context information. Based on a comparison of the received information and the goals and a target may be generated for the next day. For example, the system may generate and provide the following recommendation to achieve a glucose target, today try and work out for an additional 10 min and reduce your sugar intake by 5%. The recommendation may be calculated based on the patient specific input information, including weighting of the specific factors considered.

Athletic performance optimization implementations may incorporate one or more of the features described above. For example, a monitoring device may receive a natural language query such as, "When/what should I eat or drink to run 6 more miles (or even starting this question before the person begins to exercise, what do I need to eat/do with my insulin now to exercise in 1 hour)?" In the performance optimization context, behavioral and/or contextual inputs may include one or more of: hydration level, heart rate, target heart rate, internal temperature, outside temperature, outside humidity, analytes in the body, hydration inputs, or power output (cycling). The system may be configured to process the query using natural language processing, data mining, and/or machine learning to process the query in conjunction with the provided inputs/behavioral information. In some implementations, the query may be refined based on additional feedback, such as: expected duration of exercise, level of exertion, what did you have for breakfast, etc., carb intake. Based on the received input information, the system may be configured to generate a recommended athletic performance plan such as: drink X ounces of Y in 1 hour.

A further example of an area which may include the features described is a weight loss monitor. In this example, the monitor may receive a query (natural or structured) such as "Should I do today to meet my goal of losing weight?" or "Can you recommend restaurants or foods, servings and exercise?" The monitor may also receive physiological inputs such as glucose level, lactate, free fatty acids, heart rate during exercise and/or IgG-anti gliadin In conjunction with the physiological input, the system processes behavioral and/or contextual information (e.g., including current weight, BMI, desired weight, target calories per day (consume), target calories per day (expend), location, favorite foods, level of exertion). The processing provides a recommended schedule of activities and food based on received inputs.

Figure 7:
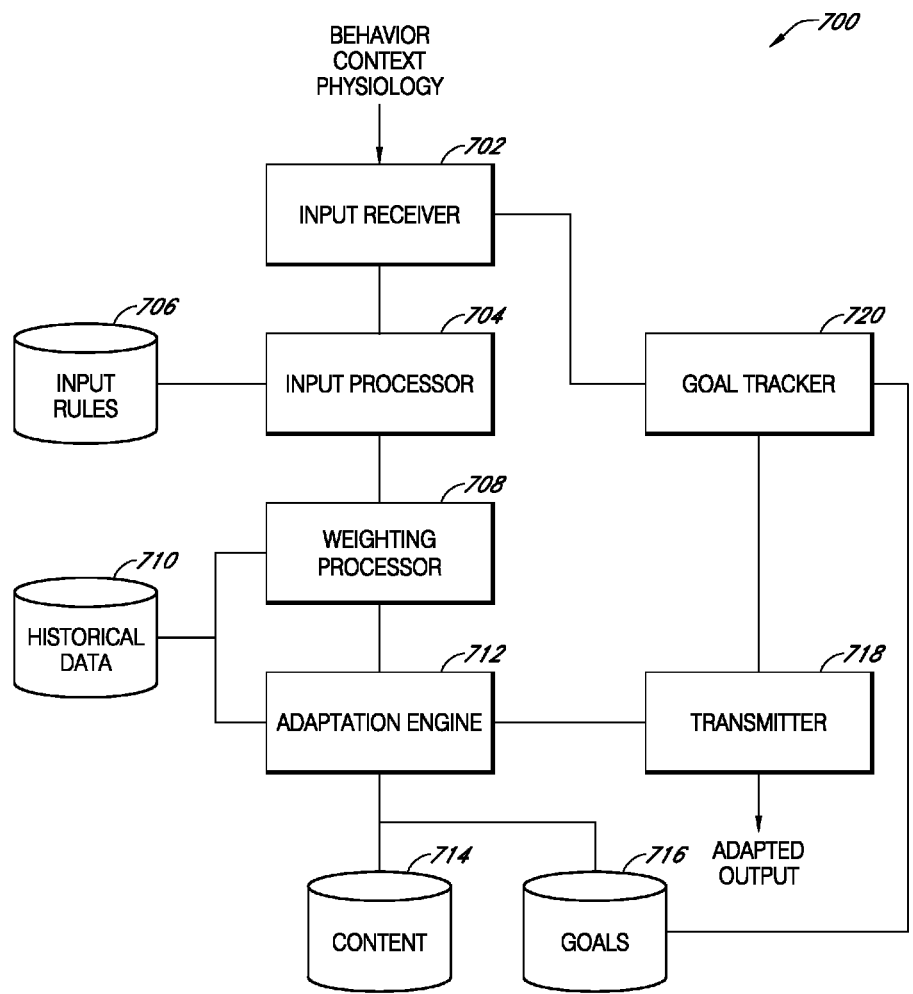
FIG. 7 is a functional block diagram for a continuous monitoring device including an adaptive interface.

FIG. 7 is a functional block diagram for a continuous monitoring device including an adaptive interface. The device 700 includes an input receiver 702. The input receiver 702 is configured to obtain behavior, context, or physiological input values. The values may be received from sensors, information systems, social media, voice response, actions on the device 700 (e.g., search), and other described above. The input receiver 702 may include wired (e.g., Ethernet, USB, HDMI, coaxial cable, telephonic, patch cabling, fiber optic cable) or wireless (e.g., WiFi, Bluetooth) communication means for obtaining the input information.

As shown in FIG. 7, the input receiver 702 is coupled with an input processor 704. The input processor 704 may be configured to process the received inputs. The input processor 704 may be configured to process the received inputs based on processing rules obtained from a processing rules database 706. The input processor 704 may receive the input data along with the source of the data. Based on the source, a processing rule may be selected from the processing rule database 706. The processing rule may indicate a format for the input data, an appropriate parser, or other information to facilitate extraction and categorization of the information included in the input data.

The input processor 704 may provide the extracted information to a weighting processor 708. The weighting processor 708 is configured to determine a weight for each value extracted from the input data. As discussed above, some inputs may influence the adaptation process more heavily than others. The weighting processor 708 is configured to identify these weights. The weighting processor 708 may be in data communication with a historical input value database 710. The historical input value database 710 includes past input values for the user. In some implementations the weighting processor 708 may transmit a request for a weighting to a remote server configured to generate the weighting based on aggregated input information for a plurality of users (e.g., big data analytics for a community of similarly situated users).

The weighted input values may be provided to an adaptation engine 712. The adaptation engine 712 is configured to identify and apply one or more of the adaptations discussed above such as device adaptations, goal adaptations, interface adaptations, training or content adaptations. The adaptation engine 712 may identify one or more adaptations included in an adaptation rules database 714. The adaptation rules database 714 may include one or more adaptations to apply based on the input value. For example, if an input value indicates low glucose, a set of adaptations may be stored in the adaptation rules database 714 indicating possible adaptations to increase glucose levels.

The adaptation engine 712 shown in FIG. 7 is in data communication with a content database 714. The content database 714 may include categorized content which is searchable based on the input values. Accordingly, a multimedia video may be stored along with a glucose threshold level (e.g., low). Based on an input glucose reading, the video may be retrieved from the content database 714 for presentation.

The adaptation engine 712 shown is also in data communication with a goal database 716. The goal database 716 may be configured to store goals and associated criteria. The goal database 716 may be configured to store template goals with pre-determined criteria. The goal database 716 may be configured to store goals for specific users or user groups. The adaptation engine 712, may identify an adaptation rule which indicates setting or adjusting an existing goal.

As shown in FIG. 7, the device 700 includes a transmitter 718. The transmitter 718 may receive the adaptations identified and transmit the changes. The transmitter 718 may include wired (e.g., Ethernet, USB, HDMI, coaxial cable, telephonic, patch cabling, fiber optic cable) or wireless (e.g., WiFi, Bluetooth) communication means for transmitting adapted information.

In some implementations, the transmitter 718 may be configured to communicate the proposed adaptation before applying the adaptation. In some implementations, the transmitter 718 may be configured to transmit the adapted message (e.g., alert, text message, email, FTP, HTTP, or other).

As shown in FIG. 7, the device 700 also includes a goal tracker 720. The goal tracker 720 is configured to determine the status of a goal based on the received input. For example, upon receipt of glucose data, the goal tracker 720 may retrieve all active goals for the user associated with the glucose data. The goal tracker 720 may then determine whether the input value received satisfies the glucose level criteria included in the identified goals. The result of the determination may be provided to the transmitter 718 for transmission. In some implementations, the transmission may include transmission of a reward as described above.

The connections between the elements shown in FIG. 7 illustrate exemplary communication paths for the device 700. Additional communication paths, either direct or via an intermediary, may be included to further facilitate the exchange of information for the device 700. The communication paths may be bi-directional communication paths allowing the elements shown to exchange information.

As used herein, the term "determining" encompasses a wide variety of actions. For example, "determining" may include calculating, computing, processing, deriving, investigating, looking up (e.g., looking up in a table, a database or another data structure), ascertaining and the like. Also, "determining" may include receiving (e.g., receiving information), accessing (e.g., accessing data in a memory) and the like. Also, "determining" may include resolving, selecting, choosing, establishing and the like.

As used herein, the term "message" encompasses a wide variety of formats for transmitting information. A message may include a machine readable aggregation of information such as an XML document, fixed field message, comma separated message, or the like. A message may, in some implementations, include a signal utilized to transmit one or more representations of the information. While recited in the singular, it will be understood that a message may be composed/transmitted/stored/received/etc. in multiple parts.

The various operations of methods described above may be performed by any suitable means capable of performing the operations, such as various hardware and/or software component(s), circuits, and/or module(s). Generally, any operations illustrated in the Figures may be performed by corresponding functional means capable of performing the operations.

The various illustrative logical blocks, modules and circuits described in connection with the present disclosure (such as the blocks of FIGS. 2 and 7) may be implemented or performed with a general purpose processor, a digital signal processor (DSP), an application specific integrated circuit (ASIC), a field programmable gate array signal (FPGA) or other programmable logic device (PLD), discrete gate or transistor logic, discrete hardware components or any combination thereof designed to perform the functions described herein. A general purpose processor may be a microprocessor, but in the alternative, the processor may be any commercially available processor, controller, microcontroller or state machine. A processor may also be implemented as a combination of computing devices, e.g., a combination of a DSP and a microprocessor, a plurality of microprocessors, one or more microprocessors in conjunction with a DSP core, or any other such configuration.

In one or more aspects, the functions described may be implemented in hardware, software, firmware, or any combination thereof. If implemented in software, the functions may be stored on or transmitted over as one or more instructions or code on a computer-readable medium. Computer-readable media includes both computer storage media and communication media including any medium that facilitates transfer of a computer program from one place to another. A storage media may be any available media that can be accessed by a computer. By way of example, and not limitation, such computer-readable media can comprise RAM, ROM, EEPROM, CD-ROM or other optical disk storage, magnetic disk storage or other magnetic storage devices, or any other medium that can be used to carry or store desired program code in the form of instructions or data structures and that can be accessed by a computer. Also, any connection is properly termed a computer-readable medium. For example, if the software is transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio, and microwave are included in the definition of medium. Disk and disc, as used herein, includes compact disc (CD), laser disc, optical disc, digital versatile disc (DVD), floppy disk and blu-ray disc where disks usually reproduce data magnetically, while discs reproduce data optically with lasers. Thus, in some aspects computer readable medium may comprise non-transitory computer readable medium (e.g., tangible media). In addition, in some aspects computer readable medium may comprise transitory computer readable medium (e.g., a signal). Combinations of the above should also be included within the scope of computer-readable media.

The methods disclosed herein comprise one or more steps or actions for achieving the described method. The method steps and/or actions may be interchanged with one another without departing from the scope of the claims. In other words, unless a specific order of steps or actions is specified, the order and/or use of specific steps and/or actions may be modified without departing from the scope of the claims.

Thus, certain aspects may comprise a computer program product for performing the operations presented herein. For example, such a computer program product may comprise a computer readable medium having instructions stored (and/or encoded) thereon, the instructions being executable by one or more processors to perform the operations described herein. For certain aspects, the computer program product may include packaging material.

Software or instructions may also be transmitted over a transmission medium. For example, if the software is transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio, and microwave are included in the definition of transmission medium.

Further, it should be appreciated that modules and/or other appropriate means for performing the methods and techniques described herein can be downloaded and/or otherwise obtained by a user terminal and/or base station as applicable. For example, such a device can be coupled to a server to facilitate the transfer of means for performing the methods described herein. Alternatively, various methods described herein can be provided via storage means (e.g., RAM, ROM, a physical storage medium such as a compact disc (CD) or floppy disk, etc.), such that a user terminal and/or base station can obtain the various methods upon coupling or providing the storage means to the device. Moreover, any other suitable technique for providing the methods and techniques described herein to a device can be utilized.

It is to be understood that the claims are not limited to the precise configuration and components illustrated above. Various modifications, changes and variations may be made in the arrangement, operation and details of the methods and apparatus described above without departing from the scope of the claims.

Unless otherwise defined, all terms (including technical and scientific terms) are to be given their ordinary and customary meaning to a person of ordinary skill in the art, and are not to be limited to a special or customized meaning unless expressly so defined herein. It should be noted that the use of particular terminology when describing certain features or aspects of the disclosure should not be taken to imply that the terminology is being re-defined herein to be restricted to include any specific characteristics of the features or aspects of the disclosure with which that terminology is associated. Terms and phrases used in this application, and variations thereof, especially in the appended claims, unless otherwise expressly stated, should be construed as open ended as opposed to limiting. As examples of the foregoing, the term 'including' should be read to mean 'including, without limitation,' 'including but not limited to,' or the like; the term 'comprising' as used herein is synonymous with 'including,' 'containing,' or 'characterized by,' and is inclusive or open-ended and does not exclude additional, unrecited elements or method steps; the term 'having' should be interpreted as 'having at least;' the term 'includes' should be interpreted as 'includes but is not limited to;' the term 'example' is used to provide exemplary instances of the item in discussion, not an exhaustive or limiting list thereof; adjectives such as 'known', 'normal', 'standard', and terms of similar meaning should not be construed as limiting the item described to a given time period or to an item available as of a given time, but instead should be read to encompass known, normal, or standard technologies that may be available or known now or at any time in the future; and use of terms like 'preferably,' 'preferred,' 'desired,' or 'desirable,' and words of similar meaning should not be understood as implying that certain features are critical, essential, or even important to the structure or function of the invention, but instead as merely intended to highlight alternative or additional features that may or may not be utilized in a particular embodiment of the invention. Likewise, a group of items linked with the conjunction 'and' should not be read as requiring that each and every one of those items be present in the grouping, but rather should be read as 'and/or' unless expressly stated otherwise. Similarly, a group of items linked with the conjunction 'or' should not be read as requiring mutual exclusivity among that group, but rather should be read as 'and/or' unless expressly stated otherwise.

Where a range of values is provided, it is understood that the upper and lower limit and each intervening value between the upper and lower limit of the range is encompassed within the embodiments.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity. The indefinite article "a" or "an" does not exclude a plurality. A single processor or other unit may fulfill the functions of several items recited in the claims. The mere fact that certain measures are recited in mutually different dependent claims does not indicate that a combination of these measures cannot be used to advantage. Any reference signs in the claims should not be construed as limiting the scope.

It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention, e.g., as including any combination of the listed items, including single members (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

All numbers expressing quantities of ingredients, reaction conditions, and so forth used in the specification are to be understood as being modified in all instances by the term 'about.' Accordingly, unless indicated to the contrary, the numerical parameters set forth herein are approximations that may vary depending upon the desired properties sought to be obtained. At the very least, and not as an attempt to limit the application of the doctrine of equivalents to the scope of any claims in any application claiming priority to the present application, each numerical parameter should be construed in light of the number of significant digits and ordinary rounding approaches.

All references cited herein are incorporated herein by reference in their entirety. To the extent publications and patents or patent applications incorporated by reference contradict the disclosure contained in the specification, the specification is intended to supersede and/or take precedence over any such contradictory material.

Headings are included herein for reference and to aid in locating various sections. These headings are not intended to limit the scope of the concepts described with respect thereto. Such concepts may have applicability throughout the entire specification.

Furthermore, although the foregoing has been described in some detail by way of illustrations and examples for purposes of clarity and understanding, it is apparent to those skilled in the art that certain changes and modifications may be practiced. Therefore, the description and examples should not be construed as limiting the scope of the invention to the specific embodiments and examples described herein, but rather to also cover all modification and alternatives coming with the true scope and spirit of the invention.

What is claimed is:

1. A method for adaptive configuration of an analyte monitoring device, the method comprising:
   measuring a glucose concentration in a host via a glucose sensor at least partially inserted in the host the glucose sensor configured to provide continuous sensor data associated with the glucose concentration in the host;
   transmitting a first report of first physiological information of the host based on the continuous sensor data using a first reporting format, wherein the first reporting format comprises a first reporting format characteristic;
   determining at least one of behavioral and contextual information comprising at least one of behavioral and contextual characteristic of the host, wherein the at least one of behavioral and contextual characteristic is associated with a physiological condition of the host;
   comparing the at least one of behavioral and contextual characteristic with one or more behavioral or contextual criteria;
   adjusting the reporting format based at least in part on said comparing, wherein the reporting format comprises a second reporting format characteristic that is different from the first reporting format characteristic, wherein the second reporting format characteristic includes a change in a level of discretion and a change in a reporting frequency; and
   transmitting a second report of second physiological information using the second reporting format.

2. The method of claim 1, wherein the first report comprises a trend graph of the first physiological information over a period of time.

3. The method of claim 1, further comprising transmitting the determined at least one of behavioral and contextual information about the host.

4. The method of claim 1, wherein determining the at least one of behavioral and contextual information comprises:
   receiving a message from a sensor including data associated with the host;
   identifying a characteristic extractor based on the message and the sensor;
   generating, via the identified characteristic extractor, the at least one of behavioral and contextual characteristic based on the received message; and
   associating the generated characteristic with the at least one of behavioral and contextual information.

5. The method of claim 1, wherein determining the at least one of behavioral and contextual information comprises:
   capturing values from pre-identified inputs, the values indicating a behavior or context associated with a physiological condition for the host;
   periodically storing additional values received from the pre-identified inputs, wherein a record of host-specific pre-identified input values is created; and
   periodically determining the at least one of behavioral and contextual information about the host based on the record of host-specific pre-identified input values captured over time.

6. The method of claim 4, wherein the pre-identified inputs include at least one of a glucometer, a thermometer, an accelerometer, a camera, a microphone, a query processing engine, an electronic device configured for machine-to-machine communication, or an electronic patient record.

7. The method of claim 4, wherein periodically storing additional values comprises storing a timestamp indicating when a specific additional value was stored.

8. The method of claim 4, wherein the physiological condition comprises one or more of diabetes, obesity, malnutrition, hyperactivity, depression, or fertility.

9. The method of claim 4, wherein determining the at least one of behavioral and contextual information comprises:
   selecting one of a plurality of pre-identified input values included in the record; and
   identifying one or more behaviors or contexts based on a comparison of the selected input value and the input providing the selected value with an identification value associated with a plurality of behaviors or contexts.

10. The method of claim 4, wherein determining the at least one of behavioral and contextual information comprises processing the pre-defined input values included in the record.

11. The method of claim 4, wherein processing the values comprises identifying a trend for the values.

12. The method of claim 1, wherein comparing the at least one of behavioral and contextual characteristic with the one or more behavioral or contextual criteria comprises comparing the at least one of behavioral and contextual characteristic with a behavioral or contextual criteria associated with a goal.

13. The method of claim 12, wherein the goal is selected from the group consisting of interaction with the device, amount of time in target, amount of time outside of target, device location, data retention, calibrating frequency, standard deviation, pattern management, time spent on certain screens, time spent hypo, time spent hyper, time spent at high rates of change, or time spent at low rates of change.

14. The method of claim 1, wherein the change in the level of discretion comprises providing a higher level of discretion based on a detection of a location of the host.

15. The method of claim 14, wherein the higher level of discretion includes providing a first level of alarms configured to discretely alert the host.

16. The method of claim 1, wherein the change in the reporting frequency comprises decreasing the frequency of alarms.

17. An electronic device for monitoring a glucose concentration in a host, the device comprising:
   a continuous glucose sensor, wherein the continuous glucose sensor is configured to substantially continuously measure the glucose concentration in the host, and to provide continuous sensor data associated with the glucose concentration in the host; and
   a processor module configured to:
      transmit a first report of first physiological information of a host based on the continuous sensor data using a first reporting format, wherein the first reporting format comprises a first reporting format characteristic;
      determine at least one of behavioral or contextual information comprising at least one of behavioral and contextual characteristic of the host wherein the at least one of behavioral and contextual characteristic is associated with a physiological condition of the host;
      compare the at least one of behavioral and contextual characteristic with one or more behavioral or contextual criteria;
      adjust the reporting format based at least in part on said comparing, wherein the reporting format comprises a second reporting format characteristic that is different from the first reporting format characteristic, wherein the second reporting format characteristic includes a change in a level of discretion and a change in a reporting frequency; and
      transmit a second report of second physiological information using the second reporting format.

18. The device of claim 17, wherein the first report comprises a trend graph of the first physiological information over a period of time.

19. The device of claim 17, wherein the processor module is configured to determine the at least one of behavioral and contextual information by:
   receiving a message from a sensor including data associated with the host;
   identifying a characteristic extractor based on the message and the sensor;
   generating, via the identified characteristic extractor, the at least one behavioral and contextual characteristic based on the received message; and
   associating the generated characteristic with the at least one behavioral and contextual information.

20. A system for adaptive configuration of an analyte monitoring device, the system comprising:
   an input receiver configured to receive at least one of first context information and first behavior information for a host over a period of time, the input receiver further configured to receive continuous sensor data from the analyte monitoring device;
   an input processor configured to identify a context or behavior based at least in part on the at least one of first context information and first behavior information received over time; and
   an adaptation engine configured to provide adaptive reporting for the analyte monitoring device based on the identified context or behavior by:
      transmitting a first report of first physiological information of the host based on the continuous sensor data using a first reporting format, wherein the first reporting format comprises a first reporting format characteristic;
      determining at least one of second behavioral and contextual information comprising at least one of behavioral and contextual characteristic of the host, wherein the at least one of behavioral and contextual characteristic is associated with a physiological condition of the host;
      comparing the at least of one behavioral and contextual characteristic with one or more behavioral or contextual criteria;
      adjusting the reporting format based at least in part on said comparing, wherein the reporting format comprises a second reporting format characteristic that is different from the first reporting format characteristic, wherein the second reporting format characteristic includes a change in a level of discretion and a change in a reporting frequency; and
      transmitting a second report of second physiological information using the second reporting format.

21. The system of claim 20, wherein the first report comprises a trend graph of the first physiological information over a period of time.

22. The system of claim 20, wherein the input processor is configured to identify at least one of a context and behavior based at least in part on the at least one of first context information and first behavior information received over time by:

receiving a message from a sensor including data associated with the host;
identifying a characteristic extractor based on the message and the sensor;
generating, via the identified characteristic extractor, the at least one of behavioral and contextual characteristic based on the received message; and
associating the generated characteristic with the at least one of behavioral and contextual information.

* * * * *

UNITED STATES PATENT AND TRADEMARK OFFICE
CERTIFICATE OF CORRECTION

PATENT NO.       : 9,953,542 B2
APPLICATION NO.  : 14/525622
DATED            : April 24, 2018
INVENTOR(S)      : Phil Mayou It is certified that error appears in the above-identified patent and that said Letters Patent is hereby corrected as shown below:

On the Title Page

Column 2 (item (56)) Line 10, change "Fredenck" to --Frederick--.

In the Specification

Column 6 Line 41, Change "adipanectin," to --adiponectin,--.

Column 13 Line 61, Change "and or" to --and/or--.

Column 23 Line 5, Change "1Og" to --10 g--.

Column 24 Line 54, Change "and or" to --and/or--.

Column 25 Line 2, Change "adipanectin," to --adiponectin,--.

Column 27 Line 60, After "record" insert --.--.

Column 32 Line 58, Change "and or" to --and/or--.

Column 36 Line 18, Change "and or" to --and/or--.

Column 36 Lines 52-53, After "exercise" insert --.--.

Column 36 Line 65, After "list" insert --.--.

Column 38 Line 41, Change "levels"" to --levels."--.

Signed and Sealed this
Tenth Day of July, 2018

Andrei Iancu
*Director of the United States Patent and Trademark Office*